(12) United States Patent
Kandegedara et al.

(10) Patent No.: US 11,633,306 B2
(45) Date of Patent: Apr. 25, 2023

(54) ABSORBENT COMPONENT

(71) Applicant: MAS Innovation (Private) Limited, Battaramulla (LK)

(72) Inventors: Deeyayawaththe Gedara Rumesh Mahela Kandegedara, Polgahawela (LK); Malnaida Marakkala Amitha Upamal, Gampaha (LK); Agampodi Shyamal Akila De Silva, Panadura (LK)

(73) Assignee: MAS INNOVATION (PRIVATE) LIMITED, Colombo (LK)

( * ) Notice: Subject to any disclaimer, the term of this patent is extended or adjusted under 35 U.S.C. 154(b) by 0 days.

(21) Appl. No.: 17/626,009

(22) PCT Filed: Sep. 7, 2020

(86) PCT No.: PCT/SG2020/050519
§ 371 (c)(1),
(2) Date: Jan. 10, 2022

(87) PCT Pub. No.: WO2021/118455
PCT Pub. Date: Jun. 17, 2021

(65) Prior Publication Data
US 2022/0249294 A1  Aug. 11, 2022

(30) Foreign Application Priority Data
Dec. 12, 2019 (GB) .................... 1918310

(51) Int. Cl.
*A61F 13/14* (2006.01)
*A41D 1/215* (2018.01)
*A61F 13/15* (2006.01)

(52) U.S. Cl.
CPC .......... *A61F 13/141* (2013.01); *A41D 1/215* (2018.01); *A61F 2013/15016* (2013.01)

(58) Field of Classification Search
CPC .......... A61F 5/451; A61F 5/453; A61F 5/455; A61F 2007/0019; A61F 2007/0021;
(Continued)

(56) References Cited

U.S. PATENT DOCUMENTS 3,840,012 A * 10/1974 Rushton, Jr. .......... A61M 1/062
450/37
4,047,534 A  9/1977 Thomaschefsky et al.
(Continued)

FOREIGN PATENT DOCUMENTS

CN  2374164 Y  4/2000
CN  101511213 A  8/2009
(Continued)

OTHER PUBLICATIONS

International Preliminary Report on Patentability in related application PCT/SG2020/050519 dated Jun. 23, 2022.
(Continued)

*Primary Examiner* — Catharine L Anderson
(74) *Attorney, Agent, or Firm* — Patterson + Sheridan, LLP

(57) ABSTRACT

The present invention generally relates to an absorbent component (100) for use in a garment. The absorbent component (100) comprises: a first layer composite (120) comprising a first foam layer (122) and a first liquid impermeable layer (124); an absorbent layer composite (140) bonded to the first liquid impermeable layer (124) for absorbing bodily fluids; and a second liquid impermeable layer (164) bonded to the absorbent layer composite (140) and first layer composite (120) to contain the bodily fluids absorbed by the absorbent layer composite (140), wherein the second liquid impermeable layer (164) forms an opening (166) for receiving the bodily fluids to the absorbent layer
(Continued)

composite (140); and wherein the first foam layer (122) is moulded to shape the absorbent component (100).

20 Claims, 18 Drawing Sheets

(58) Field of Classification Search
CPC .. A61F 13/14; A61F 13/141; A61F 13/15268; A61F 2013/15016; A61F 2013/15276
See application file for complete search history.

(56) References Cited

U.S. PATENT DOCUMENTS

| | | | |
|---|---|---|---|
| 4,125,114 A | 11/1978 | Repke | |
| 4,173,046 A | 11/1979 | Gallagher | |
| 4,193,404 A | 3/1980 | Repke et al. | |
| 4,259,958 A | 4/1981 | Goodbar | |
| 4,270,538 A * | 6/1981 | Murphy | A61M 1/062 450/37 |
| 4,700,699 A | 10/1987 | Tollerud et al. | |
| 4,875,492 A | 10/1989 | Mitchell et al. | |
| 5,017,174 A | 5/1991 | Gowrylow | |
| 5,149,336 A | 9/1992 | Clarke et al. | |
| 5,300,052 A * | 4/1994 | Kubo | A61F 5/453 604/350 |
| 5,810,796 A | 9/1998 | Kimura et al. | |
| 6,390,886 B1 | 5/2002 | Roberts | |
| 6,676,645 B1 | 1/2004 | Bitterhof | |
| 6,695,678 B1 | 2/2004 | Foley et al. | |
| 7,662,018 B1 * | 2/2010 | Thompson | A61J 13/00 604/74 |
| 7,931,633 B2 | 4/2011 | Fujikawa et al. | |
| 8,012,138 B2 | 9/2011 | Sakaguchi et al. | |
| 8,182,454 B2 | 5/2012 | Fujikawa et al. | |
| 8,628,507 B1 | 1/2014 | Carroll | |
| 9,259,038 B2 | 2/2016 | Cholet et al. | |
| 10,182,948 B2 | 1/2019 | Li | |
| 11,179,281 B2 | 11/2021 | Li | |
| 11,357,657 B2 * | 6/2022 | Yang | A41C 3/10 |
| 2008/0200096 A1 | 8/2008 | Thornton et al. | |
| 2010/0121300 A1 | 5/2010 | Hann | |
| 2015/0209196 A1 | 7/2015 | Li | |
| 2018/0055696 A1 | 3/2018 | Smith | |
| 2018/0077972 A1 | 3/2018 | Hinnershitz | |
| 2018/0168872 A1 | 6/2018 | Madden | |

FOREIGN PATENT DOCUMENTS

| | | |
|---|---|---|
| CN | 202277439 U | 6/2012 |
| CN | 202843926 U | 4/2013 |
| CN | 203015621 U | 6/2013 |
| CN | 203122776 U | 8/2013 |
| CN | 204337149 U | 5/2015 |
| CN | 204352298 U | 5/2015 |
| CN | 106726150 A | 5/2017 |
| CN | 107530208 A | 1/2018 |
| CN | 108466465 A | 8/2018 |
| EP | 0021662 A2 | 1/1981 |
| EP | 0927015 A1 | 7/1999 |
| EP | 1199056 A1 | 4/2002 |
| EP | 1626689 A1 | 2/2006 |
| EP | 1944247 A1 | 7/2008 |
| EP | 1958603 A2 | 8/2008 |
| EP | 2560593 A1 | 2/2013 |
| EP | 3508182 A1 | 7/2019 |
| GB | 2112288 A | 7/1983 |
| GB | 2449435 A | 11/2008 |
| JP | H10118112 A | 5/1998 |
| JP | 2004049764 A | 2/2004 |
| JP | 2006255385 A | 9/2006 |
| JP | 2011052333 A | 3/2011 |
| WO | 0041882 A1 | 7/2000 |
| WO | 2005034824 A1 | 4/2005 |
| WO | 2008029220 A2 | 3/2008 |
| WO | 2008142388 A1 | 11/2008 |
| WO | 2010057044 A2 | 5/2010 |
| WO | 2011114309 A1 | 9/2011 |
| WO | 2012087292 A1 | 6/2012 |
| WO | 2013180644 A1 | 12/2013 |
| WO | 2016133458 A1 | 8/2016 |
| WO | 2017192049 A1 | 11/2017 |

OTHER PUBLICATIONS

British Search Report in related application GB1918310.0 dated Jun. 4, 2020.
International Search Report and Written Opinion in related application PCT/SG2020/050519 dated Nov. 30, 2020.
Chinese Office Action in related application 22080084269.6 dated Aug. 8, 2022.
Australian Examination Report in related application AU 2020399502 dated Sep. 6, 2022.
Japanese Office Action Notification of Reasons for Refusal for related application No. 2022-504057 dated Dec. 6, 2022.

* cited by examiner

| Samples before moulding | Treated Sample | | Untreated Sample | |
|---|---|---|---|---|
| | Wetting Time (s) | Drop-in Time (s) | Wetting Time (s) | Drop-in Time (s) |
| Initial sample (before washes) | 0 | 0 | 0 | 0 |
| Sample after 5 washes | 0 | 0 | 1 | 5 |
| Sample after 10 washes | 0 | 0 | 2 | 10 |
| Sample after 25 washes | 0 | 0 | 1 | 3 |
| Sample after 50 washes | 0 | 1 | 1 | 11 |

Figure 13A

| Samples after moulding | Treated Sample | | Untreated Sample | |
|---|---|---|---|---|
| | Wetting Time (s) | Drop-in Time (s) | Wetting Time (s) | Drop-in Time (s) |
| Initial sample (before washes) | 0 | 0 | 0 | 0 |
| Sample after 5 washes | 0 | 1 | 15 | 47 |
| Sample after 10 washes | 0 | 1 | 40 | >60 |
| Sample after 25 washes | 0 | 1 | 44 | >60 |
| Sample after 50 washes | 0 | 1 | 55 | >60 |

Figure 13B

|  | Treated Sample | |
|---|---|---|
|  | Wetting Time (s) | Drop-in Time (s) |
| Initial sample (before washes, before moulding) | 0 | 0 |
| Sample after moulding (without washes) | 0 | 0 |
| Sample after 50 washes (before moulding) | 0 | 1 |
| Sample after moulding (after 50 washes) | 0 | 3 |

Figure 13C

|  | Treated Sample Absorbency Rate (s) | Untreated Sample Absorbency Rate (s) |
|---|---|---|
| Initial sample (before washes) | <1 | <1 |
| Sample after 5 washes | 3 | >60 |
| Sample after 10 washes | 16 | 45 |
| Sample after 25 washes | <1 | 3 |
| Sample after 50 washes | 10 | >60 |

Figure 13D

|  | Sample 1 | Sample 2 | Sample 3 | Sample 4 | Sample 5 |
|---|---|---|---|---|---|
| Finishing agents |  |  |  |  |  |
| RUCO®-BAC AGP | 5 g/l | 5 g/l | 5 g/l | 5 g/l | 10 g/l |
| FERAN® ICS | 30 g/l | 30 g/l | 30 g/l | 30 g/l | 30 g/l |
| RUCO®-STAD ADM | 20 g/l | - | 20 g/l | - | 20 g/l |
| RUCO-PUR SLR | - | - | 20 g/l | 20 g/l | 20 g/l |
| After 10 washes |  |  |  |  |  |
| *Staphylococcus aureus* | 99.95% | 99.21% | 99.99% | 99.85% | 99.94% |
| *Klebsiella pneumoniae* | 99.90% | 99.14% | 99.91% | 99.82% | 99.84% |
| After 50 washes |  |  |  |  |  |
| *Staphylococcus aureus* | 99.12% | 99.62% | 99.58% | 99.76% | 99.85% |
| *Klebsiella pneumoniae* | 98.45% | 99.48% | 99.57% | 99.75% | 99.78% |

Figure 13E

| Time | Absorbed amount (ml) | Obsevations |
|---|---|---|
| 0930 | 0 | No leakage observed. |
| 1030 | 5 | No leakage observed. |
| 1130 | 10 | No leakage observed. |
| 1230 | 15 | No leakage observed. |
| 1330 | 20 | No leakage observed. |
| 1430 | 25 | No leakage observed. |
| 1530 | 30 | No leakage observed. |
| 1630 | 35 | Slight leakage at outside of the absorbent component. No visible stain. Wicking surface is slightly damp. |
| 1730 | 40 | Leakage has spread over the outside of the absorbent component, but has not leaked onto the garment. Wicking surface is highly damp. |

Figure 13F

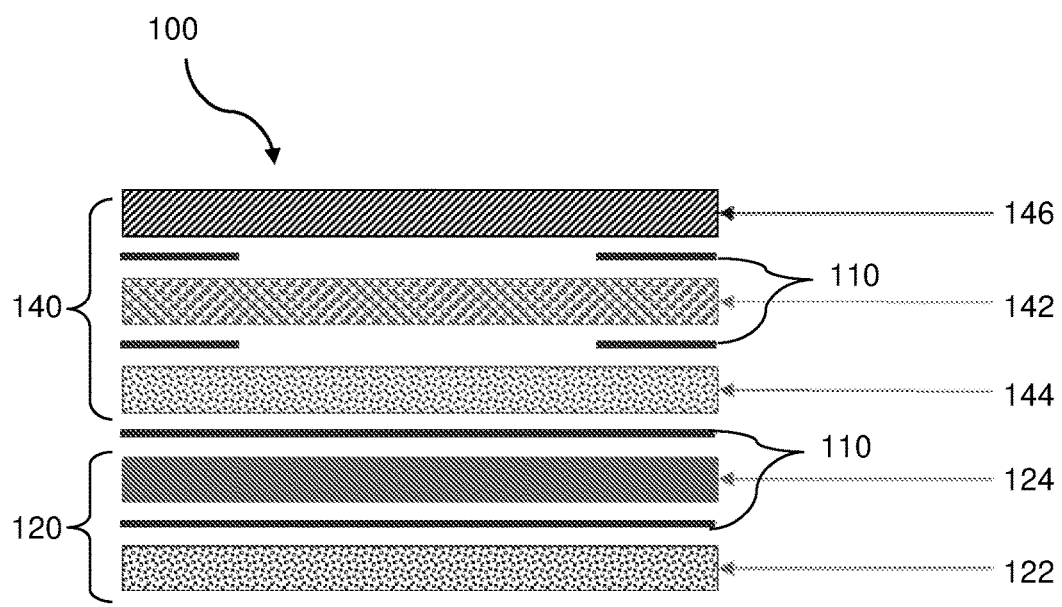

Figure 14A

ABSORBENT COMPONENT

TECHNICAL FIELD

The present invention generally relates to an absorbent component. More particularly, the present invention describes various embodiments of an absorbent component for use in a garment and a method of forming thereof, as well as a garment comprising the absorbent component and a method of forming thereof.

BACKGROUND

Absorbent garments such as reusable and washable absorbent undergarments are worn with the purpose of absorbing bodily fluids. These bodily fluids include vaginal discharge, urine, menstrual fluid, sweat, and breast milk. For nursing mothers, they often wear nursing bras which are exposed to bodily fluids such as breast milk and sweat from the breasts. Current nursing bras may use pads, such as removable absorbent nursing pads, to absorb these bodily fluids. However, the absorbent capacity of current nursing pads is low compared to the amount of breast milk leaked from the breasts through the day. The nursing pads also do not provide proper form and shape and do not stay in place within the nursing bras. Additionally, these pads are not leak-proof and feel wet when the bodily fluids leak out of the pads, making them embarrassingly visible through the clothes.

Therefore, in order to address or alleviate at least the aforementioned problem or disadvantage, there is a need to provide an improved absorbent component for use in a garment.

SUMMARY

According to a first aspect of the present invention, there is an absorbent component for use in a garment, the absorbent component comprising:
 a first layer composite comprising a first foam layer and a first liquid impermeable layer;
 an absorbent layer composite bonded to the first liquid impermeable layer for absorbing bodily fluids; and
 a second liquid impermeable layer bonded to the absorbent layer composite and first layer composite to contain the bodily fluids absorbed by the absorbent layer composite,
 wherein the second liquid impermeable layer forms an opening for receiving the bodily fluids to the absorbent layer composite; and
 wherein the first foam layer is moulded to shape the absorbent component.

According to a second aspect of the present invention, there is a method of forming an absorbent component for use in a garment, the method comprising:
 forming an unmoulded layer composite comprising:
  a first layer composite comprising a first foam layer and a first liquid impermeable layer; and
  an absorbent layer composite bonded to the first liquid impermeable layer for absorbing bodily fluids; and
 moulding the unmoulded layer composite to thereby form the absorbent component, the absorbent component comprising a second liquid impermeable layer bonded to the absorbent layer composite and first layer composite to contain the bodily fluids absorbed by the absorbent layer composite,
 wherein the second liquid impermeable layer forms an opening for receiving the bodily fluids to the absorbent layer composite; and
 wherein the first foam layer is moulded to shape the absorbent component.

According to a third aspect of the present invention, there is a garment comprising:
 a fabric body configured to be worn by a user; and
 an absorbent component for including within the fabric body, the absorbent component comprising:
  a first layer composite comprising a first foam layer and a first liquid impermeable layer;
  an absorbent layer composite bonded to the first liquid impermeable layer for absorbing bodily fluids; and
  a second liquid impermeable layer bonded to the absorbent layer composite and first layer composite to contain the bodily fluids absorbed by the absorbent layer composite,
  wherein the second liquid impermeable layer forms an opening for receiving the bodily fluids to the absorbent layer composite; and
  wherein the first foam layer is moulded to shape the absorbent component.

According to a fourth aspect of the present invention, there is a method of forming a garment, the method comprising:
 forming a fabric body of the garment configured to be worn by a user;
 forming an absorbent component for use in the garment, comprising:
  forming an unmoulded layer composite comprising:
   a first layer composite comprising a first foam layer and a first liquid impermeable layer; and
   an absorbent layer composite bonded to the first liquid impermeable layer for absorbing bodily fluids; and
  moulding the unmoulded layer composite to thereby form the absorbent component, the absorbent component comprising a second liquid impermeable layer bonded to the absorbent layer composite and first layer composite to contain the bodily fluids absorbed by the absorbent layer composite; and
 including the absorbent component within the fabric body,
 wherein the second liquid impermeable layer forms an opening for receiving the bodily fluids to the absorbent layer composite; and
 wherein the first foam layer is moulded to shape the absorbent component.

According to a fifth aspect of the present invention, there is an absorbent component for use in a garment, the absorbent component comprising:
 a first layer composite comprising a first foam layer and a first liquid impermeable layer, each of the first foam layer and the first liquid impermeable layer comprising one or more edges; and
 an absorbent layer composite bonded to the first liquid impermeable layer for absorbing bodily fluids, the absorbent layer composite comprising one or more edges,
 wherein the first liquid impermeable layer forms a liquid-impenetrable barrier between the first foam layer and the absorbent layer composite;
 wherein none of the edges of the first liquid impermeable layer extends beyond the edges of the first foam layer and the absorbent layer composite to form an edge seal; and wherein the first foam layer is moulded to shape the absorbent component.

An absorbent component for use in a garment according to the present invention is thus disclosed herein. Various features, aspects, and advantages of the present invention will become more apparent from the following detailed description of the embodiments of the present invention, by way of non-limiting examples only, along with the accompanying drawings.

BRIEF DESCRIPTION OF THE DRAWINGS

FIG. 13A to FIG. 13F are tables of test results of the absorbent component, in accordance with some embodiments of the present invention.

FIG. 14A to FIG. 14C are cross-sectional illustrations of a further absorbent component, in accordance with some embodiments of the present invention.

DETAILED DESCRIPTION

In the present invention, depiction of a given element or consideration or use of a particular element number in a particular figure or a reference thereto in corresponding descriptive material can encompass the same, an equivalent, or an analogous element or element number identified in another figure or descriptive material associated therewith. The use of "/" in a figure or associated text is understood to mean "and/or" unless otherwise indicated. The recitation of a particular numerical value or value range herein is understood to include or be a recitation of an approximate numerical value or value range. As used herein, the terms "first", "second", and "third" are used merely as labels or identifiers and are not intended to impose numerical requirements on their associated terms.

For purposes of brevity and clarity, descriptions of embodiments of the present invention are directed to an absorbent component for use in a garment, in accordance with the drawings. While aspects of the present invention will be described in conjunction with the embodiments provided herein, it will be understood that they are not intended to limit the present invention to these embodiments. On the contrary, the present invention is intended to cover alternatives, modifications and equivalents to the embodiments described herein, which are included within the scope of the present invention as defined by the appended claims. Furthermore, in the following detailed description, specific details are set forth in order to provide a thorough understanding of the present invention. However, it will be recognized by an individual having ordinary skill in the art, i.e. a skilled person, that the present invention may be practiced without specific details, and/or with multiple details arising from combinations of aspects of particular embodiments. In a number of instances, well-known systems, methods, procedures, and components have not been described in detail so as to not unnecessarily obscure aspects of the embodiments of the present invention.

Figure 1A:
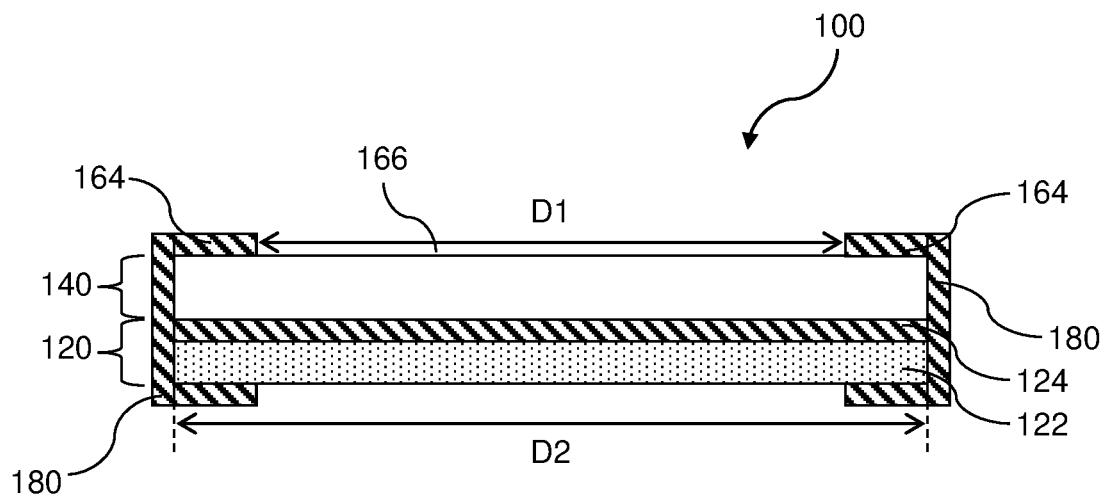
FIG. 1 to FIG. 5 are cross-sectional illustrations of an absorbent component, in accordance with various embodiments of the present invention.
Figure 2:
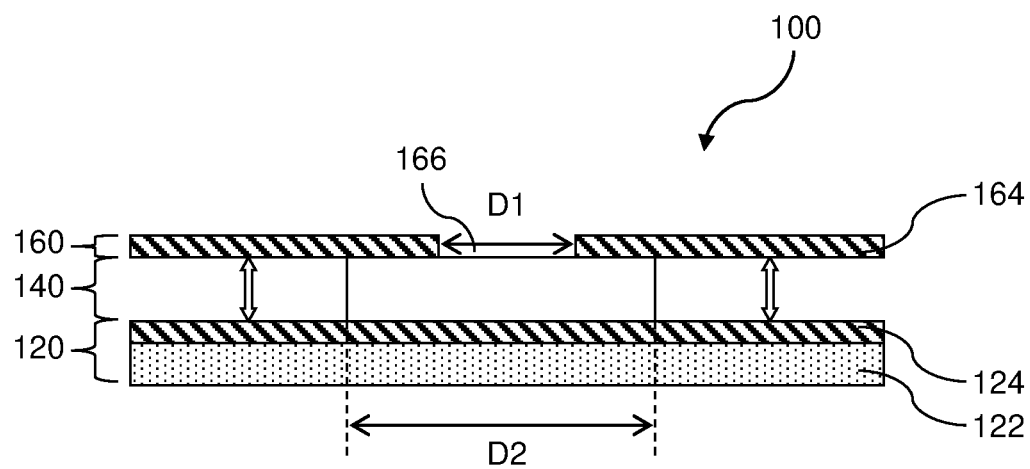

In representative or exemplary embodiments of the present invention, there is an absorbent component 100 for use in a garment as illustrated in FIG. 1A and FIG. 2. The garment may be a maternity garment, postpartum garment, or female undergarment, particularly one that is worn over the breast. For example, the absorbent component 100 is useable in a postpartum garment such as a nursing bra for absorbing bodily fluids such as breast milk and sweat, preventing leakage of the bodily fluids through the garment.

The absorbent component 100 includes a first layer composite 120 and an absorbent layer composite 140 bonded to the first layer composite 120. As used herein, the term "layer composite" is defined as having one or more layers bonded together. The first layer composite 120 includes a first foam layer 122 and a first liquid impermeable layer 124 bonded to the first foam layer 122. The absorbent layer composite 140 is bonded to the first liquid impermeable layer 124 and is arranged for absorbing liquid, particularly bodily fluids. The absorbent component 100 further includes a second liquid impermeable layer 164 bonded to the absorbent layer composite 140 and to the first layer composite 120 to contain the bodily fluids absorbed by the absorbent layer composite 140.

The second liquid impermeable layer 164 forms an opening 166 for receiving the bodily fluids to the absorbent layer composite 140. The opening 166 has an overall dimension D1. In some embodiments, the shape of the opening 166 may be circular and the circular opening 166 has a diameter D1. In some other embodiments, the opening 166 may be of other symmetrical or asymmetrical shapes such as a square, rectangle, oval, or triangle having an overall width D1. The opening 166 is formed such that a liquid, such as bodily fluids from the user wearing the garment, is able to communicate through the opening 166 to the underlying absorbent layer composite 140. The opening 166 is positioned in the absorbent component 100 to match the position of the body part excreting or discharging the bodily fluids. For example, the garment including the absorbent component 100 is worn on the breast, and the opening 166 is positioned at the nipple area where there may be leakage of breast milk. The opening 166 may be positioned at the centre of the absorbent component 100, or may be positioned offset from the centre, as nipples may be located at different areas of the breasts for different women.

The absorbent layer composite 140 is bonded to the first layer composite 120 and to the second liquid impermeable layer 164, for absorbing the bodily fluids received through the opening 166. The absorbent layer composite 140 has an overall dimension D2 that is larger than D1, such that the absorbent layer composite 140 is bonded to the second liquid impermeable layer 164 and covers the opening 166. In some embodiments, the shape of the absorbent layer composite 140 may be circular and the circular absorbent layer composite 140 has a diameter D2. In some other embodiments, the absorbent layer composite 140 may be of other symmetrical or asymmetrical shapes such as a square, rectangle, oval, or triangle having an overall width D2. The absorbent layer composite 140 includes one or more layers of absorbent material having a suitable collective absorbent capacity to absorb leakage of bodily fluids from the user over a period of time. For example, the collective absorbent capacity of the absorbent layer composite 140 is at least 30 ml.

The combination of the layer composites 120,140 are moulded together to form the absorbent component 100. As a result of the moulding, the second liquid impermeable layer 164 are bonded to the absorbent layer composite 140 and the first layer composite 120 to contain the bodily fluids absorbed by the absorbent layer composite 140 from the opening 166. Specifically, the liquid impermeable layers 124,164 form a liquid impermeable seal or barrier substantially around the absorbent layer composite 140 to prevent leakage of the bodily fluids through the absorbent layer composite 140. This advantageously avoids embarrassment to the user as the bodily fluids do not leak out into the garment including the absorbent component 100.

Additionally, as a result of the moulding, the first foam layer 122 is moulded to shape the absorbent component 100. Specifically, the absorbent component 100 is moulded and shaped to conform to the body part on which the garment including the absorbent component 100 is worn. For example, the garment is a nursing bra and the moulded absorbent component 100 is shaped to conform to the breast shape. The absorbent component 100 thus achieves a structured shape that allows it to lie substantially flat when used in the garment, making it less visible from outside the garment. The reduced visibility of the absorbent component 100 through the garment or clothing avoids embarrassment to the user and expands clothing options for the user.

Figure 1B:
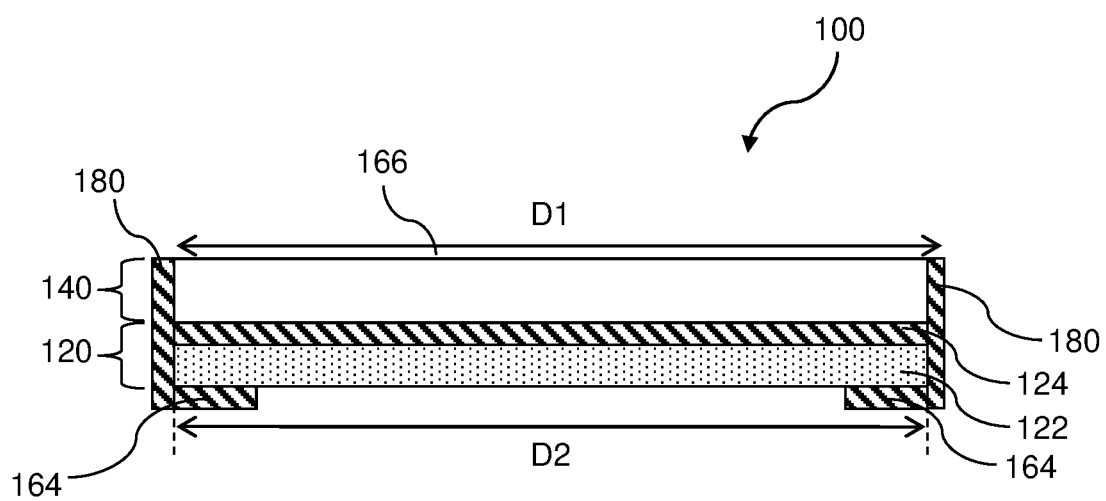
Figure 1C:
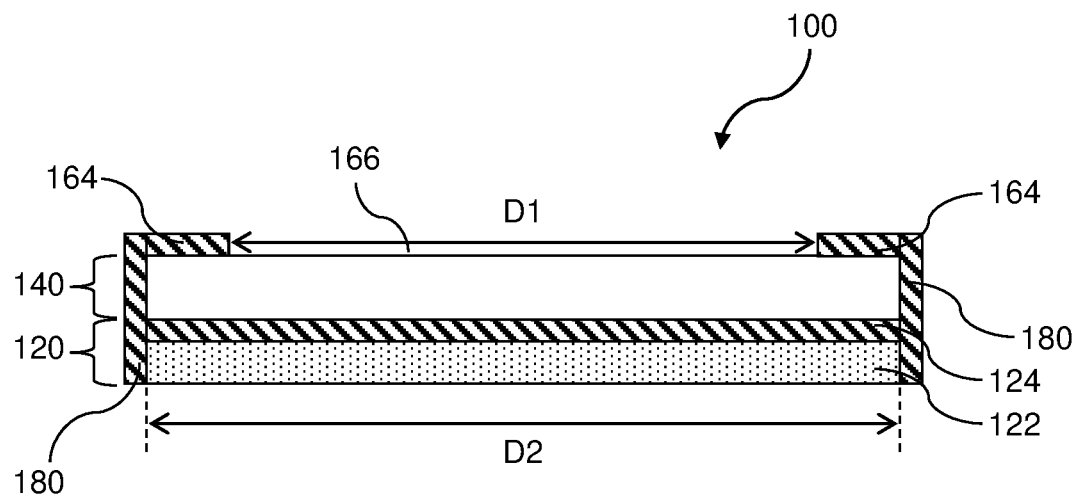
Figure 1D:
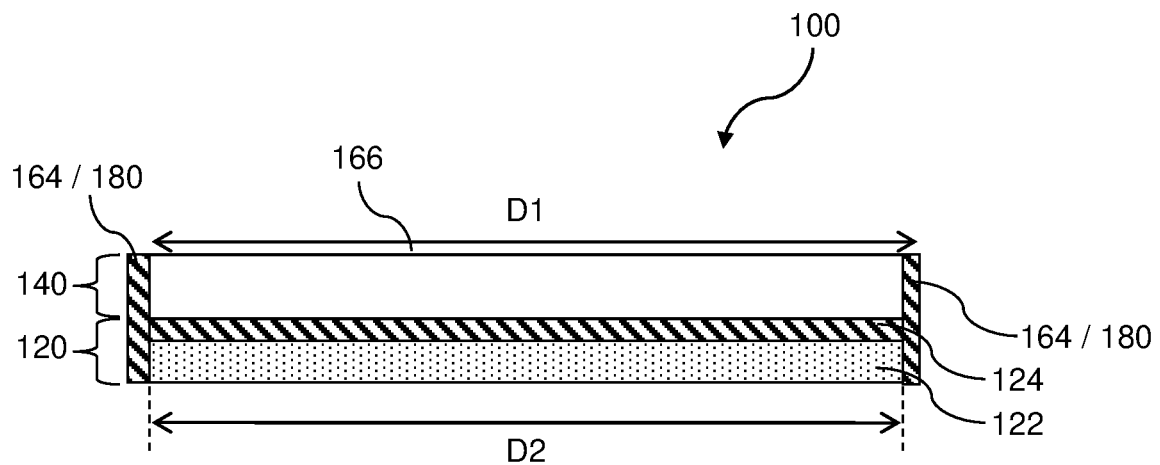

In some embodiments as shown in FIG. 1A, the first layer composite 120 and absorbent layer composite 140 have approximately the same overall dimensions, such as the same length, width, and/or diameter. The second liquid impermeable layer 164 is bonded to the absorbent layer composite 140 and the first foam layer 122 to form a peripheral liquid impermeable barrier 180 around the absorbent component 100. For example as shown in FIG. 1A, the peripheral liquid impermeable barrier 180 is formed by the second liquid impermeable layer 164 arranged in a C-shaped manner. It may alternatively be formed by multiple portions of the second liquid impermeable layer 164 joined together in a C-shaped manner. The second liquid impermeable layer 164 may be formed around the absorbent component 100 in other manners, such as an L-shaped manner as shown in FIGS. 1B and 1C or a straight manner as shown in FIG. 1D. The second liquid impermeable layer 164 may further be bonded to the first liquid impermeable layer 124. The liquid impermeable layers 124,164 are thus bonded together to prevent leakage of bodily fluids from the absorbent layer composite 140.

In some embodiments as shown in FIG. 2, the absorbent layer composite 140 has smaller overall dimensions than the first layer composite 120. The second liquid impermeable layer 164 is bonded to the absorbent layer composite 140 and the first liquid impermeable layer 124 to form a leakproof pocket containing or enclosing the absorbent layer composite 140. The absorbent component 100 may include a second layer composite 160 that includes the second liquid impermeable layer 164.

Figure 3:
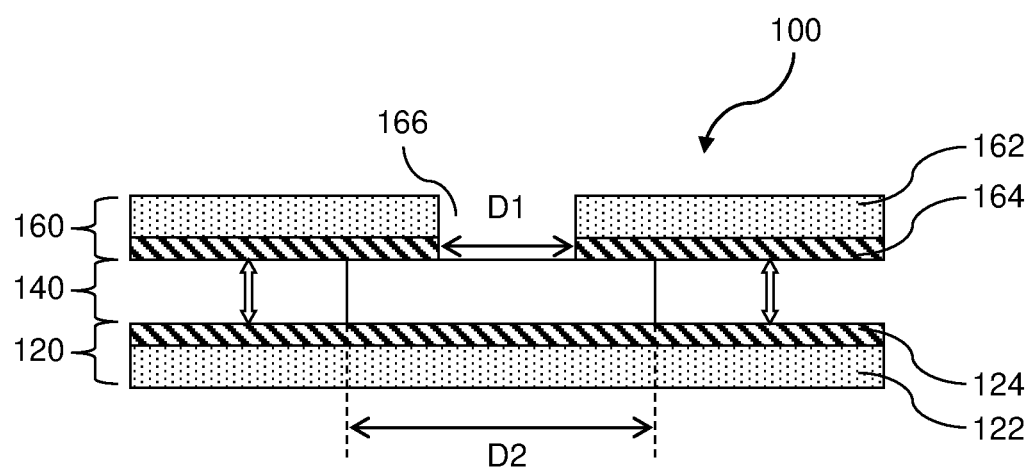
Figure 4:
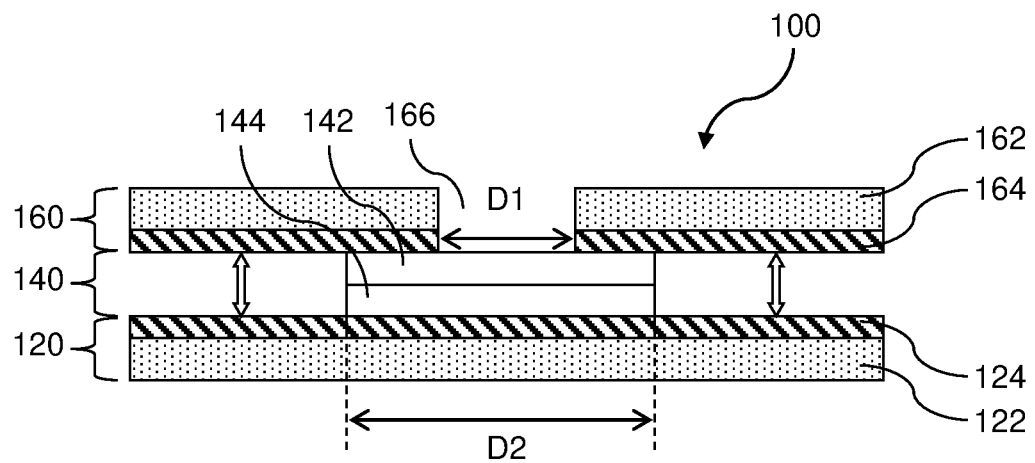
Figure 5:
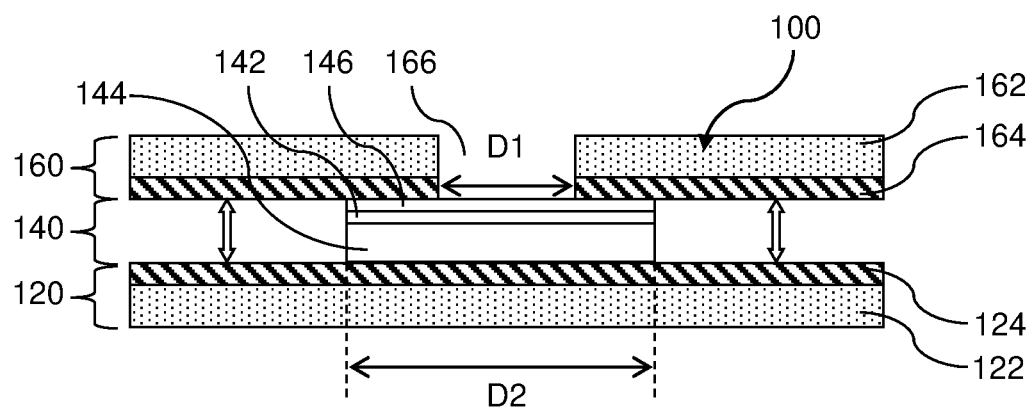

In some variations as shown in FIG. 3 to FIG. 5, the second layer composite 160 may further include a second foam layer 162, wherein the opening 166 is formed through the second foam layer 162 and second liquid impermeable layer 164. The second layer composite 160 is bonded to the absorbent layer composite 140 at the second liquid impermeable layer 164, such that the absorbent layer composite 140 interposes the first layer composite 120 and the second layer composite 160. The combination of the layer composites 120,140,160 are moulded together to form the absorbent component 100. As a result of the moulding, the second foam layer 162, together with the first foam layer 122, is moulded to shape the absorbent component 100, allowing the absorbent component 100 to achieve a structured shape.

In some embodiments, the absorbent layer composite 140 includes an absorbent layer made of a suitable liquid absorbent/absorbing material known in the art and that is able to achieve the desired absorbent capacity, such as at least 30 ml. The liquid absorbent/absorbing material may be cotton, a cotton blend, foam, a synthetic material, absorbent polymeric foam, a nanotechnology-based or nanotechnology-produced material, or any other moisture-absorbent material. For example, the absorbent layer may be made from an 80:20 blend of polyester:nylon fabric with a microfiber double terry knit. Other suitable materials include polypropylene or any cellulose-based fabric and their blends including cotton, bamboo etc.

The absorbent layer may be subjected to a special chemical treatment on the outer surface thereof, i.e. the outer surface interfacing with the opening 166, such that it enables liquid to be transported efficiently to the absorbent core material. Such chemical treatments will be readily known to the skilled person. The absorbent layer may be made from a blended fibre comprising two or more of superabsorbent polymer (SAP), hydrogel and polyester, or at least part (e.g. the outer surface interfacing with the opening 166) of the absorbent layer may have been treated with SAP and/or hydrogel. The absorbent layer may be made from a reusable superabsorbent polymer material, which may be fibrous or non-fibrous, for absorbing liquids. Particularly, when the superabsorbent polymer absorbs the liquid, it converts to a gel and revers to its original form when the absorbed liquid is removed, i.e. after the absorbent layer dries. In these embodiments, the use of these materials may result in increased liquid absorbent capacity with a reduced thickness and weight, and in an improved dry feel on the outer surface in contact with the user's skin, due to an increased affinity in the absorbent layer.

In some embodiments, the absorbent layer is an absorbent fabric layer 142 made of an absorbent fabric material. The absorbent fabric material is preferably a synthetic fabric material to withstand the high temperature of the moulding process. For example, the absorbent fabric material is a 100% polyester double terry fabric. This material is approximately 90% air and so allows for a higher absorbent capacity, as moisture fills up the air gaps of the polyester terry fabric without significant expansion of the polyester fibres. This does not translate into significantly thicker absorbent fabric layer 142.

The absorbent fabric layer 142 would be in direct contact with the user's skin, e.g. at breast/nipple, and is able to absorb the bodily fluids easily. The fibre surface of the absorbent fabric layer 142 is first wetted by the bodily fluids and communicated or transported into the voids between the fibres. The bodily fluids are then absorbed into the fibres and diffused. The fabric loops of the absorbent fabric layer 142, e.g. French Terry loops, allow the bodily fluids to be communicated to the underlying absorbent fabric material for increased absorption.

The absorbent fabric material may be determined based on various factors, including the fabric/pile density, yarn characteristics, fabric structure, surface and structure porosity, and finishing treatments. Examples of absorbent fabric materials include French Terry fabrics with piles on a single side or both sides of the absorbent fabric layer 142. The height of the pile can be adjusted and they can absorb well due to greater surface area of piles. The absorbent fabric layer 142 may be woven, knitted, or non-woven and the material may include natural fibres such as bamboo, hemp, modal, and the like. Spacer fabrics may also be incorporated in the absorbent fabric layer 142 for shaping the absorbent component 100.

In some embodiments, the absorbent layer is an absorbent foam layer 144 made of an absorbent foam material. The absorbent foam material further allows the absorbent layer composite 140 to be moulded to thereby shape the absorbent component 100. The absorbent foam material may be a polyurethane/polyurethane-based foam composition or a non-polyurethane/non-polyurethane-based water absorbent polymer foam composition. Polyurethane foams are also used in sponges and for other uses that require high liquid absorption properties, such as specialty packaging and personal care and hygiene items, including highly absorbent diapers. Non-polyurethane water absorbent polymer foam compositions include a water-insoluble, water-swellable polymer composition having a copolymer of styrene and maleic anhydride and a multi-arm block copolymer of styrene and ethylene oxide.

The absorbent foam material may be a superabsorbent foam, such as polyurethane or polyisocyanurate resins. The superabsorbent foam may be produced by incorporating superabsorbent materials, such as fibres or powders, into a conventional foam formulation, optionally in the presence of alkylene carbonate such as propylene carbonate. The superabsorbent foam may be used in conventional foam applications, such as sponges, personal hygiene products, diapers, etc. where high absorbency of liquids is desired. The absorbent foam material may be a water-absorbent, predominantly open-cell foam based on cross-linked acid-functional monomers. These are produced for example by foaming a polymerizable aqueous mixture which has at least 50 mol % of neutralized acid-functional monoethylenically unsaturated monomer, cross-linker, and at least one surfactant, and subsequently polymerizing the foamed mixture. The foam may optionally be subjected to surface post-crosslinking by spraying a cross-linker onto the foamed material or immersing the foam therein and heating the cross-linker-laden foam to a higher temperature.

Any suitable shape of absorbent foam (e.g. super absorbent foam) may be used in embodiments of the invention. A particular shape that may be mentioned herein that may be useful is one in which the absorbent foam has its sides shaved in an angular manner to provide a trapeze shape (i.e. the surface footprint on the side facing towards a user is larger than the surface footprint facing away from the user). Without wishing to be bound by theory, it is believed that this type of shape may direct fluid to the centre of the absorbent component, thereby reducing the chance of leaks at the edges of the absorbent component 100—especially in a component that does not contain an edge seal, as described in more detail hereinbelow.

In some embodiments as shown in FIG. 4, the absorbent layer composite 140 includes the absorbent fabric layer 142 and absorbent foam layer 144, wherein the absorbent fabric layer 142 is bonded to the second layer composite 160. Specifically, the absorbent fabric layer 142 interposes the second liquid impermeable layer 164 and absorbent foam layer 144. The absorbent fabric layer 142 and absorbent foam layer 144 are bonded together with bonding means 110. The bonding means 110 is applied at peripheral portions of the absorbent fabric layer 142 and absorbent foam layer 144 around the opening 166 so that the bodily fluids are able to communicate from the opening 166 through the absorbent layer composite 140.

In some embodiments, the absorbent layer composite 140 includes at least one of the absorbent fabric layer 142 and/or absorbent foam layer 144, as well as a wicking layer 146 bonded to the second liquid impermeable layer 164 and interfacing with the opening 166. Specifically, the wicking layer 146 interposes the second liquid impermeable layer 164 and absorbent fabric layer 142/absorbent foam layer 144.

The wicking layer 146 and absorbent fabric layer 142/absorbent foam layer 144 are bonded together with bonding means 110. The bonding means 110 is applied at peripheral portions of the respective layers around the opening 166 so that the bodily fluids are able to communicate from the opening 166 through the absorbent layer composite 140.

In some embodiments, the absorbent layer composite 140 includes the absorbent fabric layer 142 and wicking layer 146 on the surface of the absorbent fabric layer 142. The absorbent fabric layer 142 may be made of modified spacer fabrics and the wicking layer 146 transports liquids into the absorbent layer composite 140 for absorption by the spacer fabrics. The mono filaments used in the spacer fabrics may be replaced, or used in addition with, absorbent yarns for absorption of liquids.

Figure 6:
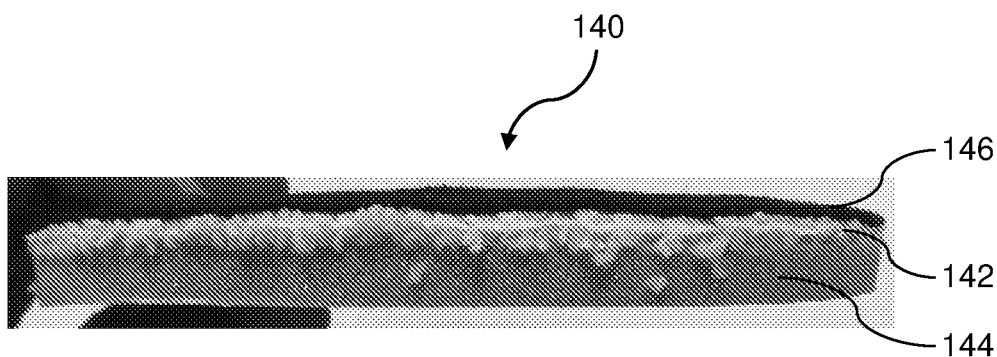
FIG. 6 is a cross-sectional illustration of an absorbent layer composite of the absorbent component, in accordance with some embodiments of the present invention.

In some embodiments as shown in FIG. 5 and FIG. 6, the absorbent layer composite 140 includes the absorbent fabric layer 142, absorbent foam layer 144, and wicking layer 146. The wicking layer 146 interfaces with the opening 166 and interposes the second liquid impermeable layer 164 and absorbent fabric layer 142. The absorbent fabric layer 142 interposes the wicking layer 146 and absorbent foam layer 144. The overall dimensions of each of the absorbent fabric layer 142, absorbent foam layer 144, and wicking layer 146 may be the same or may be different. For example, the wicking layer 146 may have smaller overall dimensions than the underlying absorbent fabric layer 142 and absorbent foam layer 144. Alternatively, the middle absorbent fabric layer 142 may have smaller overall dimensions than the absorbent foam layer 144 and wicking layer 146.

The arrangement of the wicking layer 146 enables the bodily fluids to be transported efficiently to the underlying absorbent fabric layer 142 and/or absorbent foam layer 144, resulting in an improved dry feel on the surface of the wicking layer 146 in contact with the user's skin, due to an increased affinity in the absorbent fabric layer 142/absorbent foam layer 144. Since the wicking layer 146 has direct contact with the user's skin, it is able to absorb the bodily fluids with ease. The knitted loops, such as terry loops, on the wicking layer 146 allow for the bodily fluids to be transferred throughout the underlying absorbent fabric layer 142/absorbent foam layer 144, allowing for increased absorption. The combination of the absorbent fabric layer 142/absorbent foam layer 144 with the wicking layer 146 enhances liquid transport and absorption and increases the absorbent capacity of the absorbent layer composite 140, such as at least 30 ml.

The wicking layer 146 is capable of acquiring and distributing liquid to the absorbent fabric layer 142/absorbent foam layer 144. Specifically, when the garment including the absorbent component 100 is worn by the user, the wicking layer 146 faces the user's body and serves to transport bodily fluids produced by the user's body to the absorbent fabric layer 142/absorbent foam layer 144. In other words, the wicking layer 146 transports liquid from its outer surface that is in direct contact with the user's skin to its internal surface that is in contact with the absorbent fabric layer 142/absorbent foam layer 144.

The wicking layer 146 is preferably made of a synthetic fabric material to withstand the high temperature of the moulding process. The wicking layer 146 may be made from fibres or yarns made with fibres, where said fibres and yarns are selected from one or more of the group consisting of polyamide, polyester, polyolefin, polyurethane, polyacrylonitrile, natural cellulose, regenerated cellulose, regenerated cellulose derivatives (i.e. cellulose acetate and cellulose triacetates), natural protein and regenerated protein. The wicking layer 146 may be produced using technologies such as knitting (warp knitting such as raschel Tricot, weft knitting such as circular or flat), weaving, non-woven methods (blow spinning, staple nonwoven, spun laid, air-laid, needle punched, thermal bonded, hydro-entangled, chemical bonded and so forth), electro-spinning, force-spinning etc. Additionally, the wicking layer 146 may also include one or more of the coatings, treatments encapsulation or entrapments, which would enhance its liquid and moisture management functionality, such as rate of wicking, wicking capacity, rate of spreading and distribution, one-way liquid transport etc.

The material of the wicking layer 146 may be naturally moisture-wicking and/or be treated to become moisture-wicking. For example, the wicking material may be 100% polyester fabric with French Terry knit and a denier differential across the two faces of the wicking layer 146 that assists in moving the liquid from the skin-facing side of the wicking layer 146 to the internal surface that is in contact with the absorbent fabric layer 142/absorbent foam layer 144. Other suitable wicking materials include blends of polyester, polypropylene and cotton. An advantage associated with the use of a wicking layer 146 having the triangular ridge structures/3D textured surfaces of French Terry/double jersey knitting facing the user's skin is that less surface area of the surface of the wicking layer 146 comes into contact with the user's skin and therefore reduces any sensation of feeling wetness against the skin.

In some embodiments, the wicking layer 146 includes material that is 51% cotton and one or both of the inner and outer surfaces of the wicking layer 146 may be treated with a hydrophilic composition or material (e.g. polyethylene oxide, polyvinyl alcohol, polyacrylamide, poly acrylic acid, polyvinyl pyrrolidone, hydrophilic silicones, or hydrophilic polyurethanes) and/or a hydrophobic composition or material (e.g. silicones, polyfluoroalkylacrylates, polyacrylates, polyurethanes, or waxes) to create a net hydrophilic gradient over the wicking layer 146. In other words, the surface in direct contact with the user's skin may be less hydrophilic (i.e. more hydrophobic) whereas the outer surface may be more hydrophilic. For example, the surface of the wicking layer 146 in direct contact with the user's skin may be treated with a hydrophobic material and/or the opposing surface may be treated with a hydrophilic material. This results in a combination of a "pushing" force generated by the hydrophobic properties of the surface in direct contact with the user's skin and a "pulling" force generated by the hydrophilic properties of the outer surface that may wick any moisture or liquid through the wicking layer 146 and away from the user. The hydrophilic and hydrophobic compositions may be applied to the wicking layer 146 using any conventional method known to the skilled person.

Additionally, the differential capillary forces on either side can be created by the fabric structure of the wicking layer 146 where one side of the wicking layer 146 has a smaller pore size in comparison to the opposite side of the wicking layer 146. Preferably, this pore combination creates funnel-like structures through the wicking layer 146 in cross-section, where the liquid is pulled from the side with the larger pore size to the side with the smaller pore size, due to the differential capillary pressure. The fabric structure of the wicking layer 146 may enable the liquid to pass through and spread across a wider area of the underlying absorbent fabric layer 142 and/or absorbent foam layer 144. This helps to utilize the maximum area from the absorbent fabric layer 142 and/or absorbent foam layer 144 to achieve a higher absorbent capacity.

The rate of wicking through the wicking layer 146 may be controlled to be faster or slower. The rate may be set at a maximum rate of absorption of the wicking layer 146 to ensure that all, or a significant percentage of, the liquid is absorbed by the absorbent layer 146 and does not leak beyond the confines of the absorbent component 100. The rate of wicking may be controlled by the density, thickness, or composition of the wicking layer 146 and/or by the amount and type of hydrophobic and/or hydrophilic material applied to the wicking layer 146. In another embodiment, the rate of wicking may be set such that the outer surface of the wicking layer 146 in direct contact with the user feels dry or mostly dry to the user while the other surface may feel wet.

In some embodiments, the wicking layer 146 may include an anti-microbial finishing agent, compound, or substance. For example, the anti-microbial agent may be one or more agents selected from the group consisting of a silver-containing agent, copper-containing agent, titanium dioxide, a quarternary silane, hydrogen peroxide, triclosan and zinc pyrithione. The anti-microbial finishing agent may be non-biocidal and skin-friendly, such as non-leaching non-toxic silver-containing anti-microbial agent, to ensure safety of the absorbent component 100. As the absorbent component 100 may be used in postpartum garments, such as in nursing bras, the absorbent component 100 would be in direct contact with the mother's breast. The non-biocidal agent avoids killing good bacteria on the mother's skin that would be beneficial to the baby when the baby is being breastfed. The anti-microbial finishing agent that is non-biocidal and skin-friendly is thus safe for both mother and baby.

Additionally or alternatively, the wicking layer 146 may include an agent, compound, or substance that combats odour. This finishing agent combats odour by preventing or reducing adherence of bacteria to the fabric surface and by capturing the odour molecules released by the bacteria. For example, the agent that combats odour may be one or more agents selected from the group consisting of nanoparticles with acid-neutralising pockets, high surface area mineral compositions, high surface area ceramic compositions and high surface area clay compositions. A non-limiting example of a finishing agent to combat odour is functionalized silane. Further additionally or alternatively, the wicking layer 146 may include a stain-resistant or stain-proof component.

It will be appreciated that one or more or all the layers of the absorbent layer composite 140 may include one or more of the anti-microbial agent, anti-odour agent, and antistaining agent as described above for the wicking layer 146. It will also be appreciated instead of adding such agents, suitable materials having inherent properties of such agents may be used. For example, suitable fabrics with an anti-microbial material embedded or integrated into the yarns may be used instead of adding an anti-microbial finishing agent, such as during yarn extrusion or yarn manufacturing process.

As the absorbent component 100 is subjected to a moulding process, the heat from the moulding process may weaken the functionalities of the wicking layer 146. To mitigate this problem, the wicking layer 146 may be treated with a wicking agent. The wicking agent allows the wicking layer 146 to withstand the moulding conditions, including temperature, pressure, and dwell time. The wicking agent maintains the functionalities of the wicking layer 146 with minimal changes to the fabric material and structure of the wicking layer 146. The wicking agent enhances the wicking rate of the wicking layer 146 after the moulding process, allowing the user to feel dry at all times.

One example of the wicking agent is a non-ionic ethoxylated carboxylic acid compound, such as FERAN® ICE. This compound can be used as hydrophilic finishing agent for pad or exhaust applications and is resistant of mild washing. Additionally, this compound renders a softening effect to woven, non-woven, and knitted fabrics made from synthetic fibres, especially polyester or PES fibres or their blends with cellulosic fibres. Properties of this compound include conferring good hydrophilic and absorptive properties, improving anti-static properties of the textile/fabric, a hydrophilic finishing effect on synthetic fibres, resistance to mild washing, minimal change of shade of the textile/fabric, minimal yellowing of the textile/fabric if separately applied, Bluesign® approved, and suitable for WEKO fluid application (WFA).

In some embodiments, the absorbent layer composite 140 further includes an outer softening layer disposed over the wicking layer 146/absorbent fabric layer 142/absorbent foam layer 144. This outer softening layer would be in direct contact with the user's skin and provides a softening/moisturizing finish to address skin sensitivity, particular nipple sensitivity, thereby improving comfort to the user when the garment including the absorbent component 100 is worn on the breast.

As described in some embodiments above, the first layer composite 120 includes the first foam layer 122 and first liquid impermeable layer 124, and the second layer composite 160 includes the second foam layer 162 and second liquid impermeable layer 164. The foam layers 122,162 may be made of polyurethane foam, such as polyol and isocyanate which are derived from crude oil. The foam layers 122,162 are moulded to shape the absorbent component 100, thereby achieving the required shape after the moulding process, such as to conform to the breast shape.

Each of the foam layers 122,162 may be laminated on one side. The lamination gives a smooth outer appearance or finish and allows for added comfort on the user's skin. The lamination may be done with woven or knitted fabrics, and preferably of a synthetic fabric material to withstand the high temperature of the moulding process. Knitted fabrics may be used due to better stretchability which is similar to that of foam. Some examples of knitted fabrics include polyethylene terephthalate (PET), nylon, a combination of PET and nylon and an elasticized blend, a combination of PET and the elasticized blend, and a combination of cotton and the elasticized blend. The elasticized blend may be Spandex, Lycra, or elastane. The fabric lamination may have any structure, but an interlocking fabric structure is preferred due to its balanced, smooth, stable structure that lies flat without curling and to avoid the visibility of the foam layers 122,162 through the holes after moulding. Double jersey fabrics like interlock fabrics also have higher cover factors, which represents the ratio of the area covered by yarns to the area covered by the fabric. Alternatively, spacer fabrics can also be added to the foam layers 122,162 after the moulding process to contribute to the desired shape of the absorbent component 100. Particularly, these spacer fabrics help to support the form and shape of the moulded foam layers 122,162, thereby improving the overall form and shape of the absorbent component 100.

In some embodiments, instead of the one-sided laminated foam layers 122,162, the foam layers 122,162 may be made of an absorbent foam material, such as those described above for the absorbent foam layer 144. The absorbent foam layers 122,162 provides absorbent capacity for bodily fluids that may leak from the body around the opening 166, as well as to provide shape to the absorbent component 100 after moulding.

In some embodiments, the foam layers 122,162 may be made of a stretchable or elastic foam material. For example, the foam layers 122,162 are made of a four-way stretch foam material which is stretchable to accommodate breast size fluctuations during breastfeeding.

Each of the liquid impermeable layers 124,164 may include any wholly or partially liquid-blocking material that is known. Preferably, the liquid impermeable layers 124,164 are breathable, so that liquid may not pass through them, but gases (including water vapour) can do so. For example, the liquid impermeable layers 124,164 may include one or more layers of a thermoplastic or thermoset film, where the thermoplastic or thermoset film is selected from one or more of the group consisting of polyurethane, polyester, polyolefin and silicone. Particular examples of liquid impermeable materials include layers made from a liquid impermeable polymer or a thermoplastic polyurethane film. The liquid impermeable layers 124,164 may be thermoplastic polyurethane elastomer tapes such as Mobilon tapes.

In some embodiments, the liquid impermeable layers 124,164 may be a lightweight tightly knitted/woven fabric coated with SAP/hydrogel, or may be a lightweight tightly knitted/woven fabric made using textile/SAP hybrid fibres. Alternatively, the liquid impermeable layers 124,164 may be a liquid-proof membrane. When used in the absorbent component 100, the liquid impermeable layers 124,164 may provide the advantage of being fully breathable in dry form, while providing an effective barrier material upon exposure to liquid. Furthermore, these materials may also enable the absorbent component 100 to dry more quickly than the use of a liquid impermeable polymer such as a thermoplastic polyurethane film.

In some embodiments, one or both liquid impermeable layers 124,164 is a single-sided or double-sided adhesive layer or film having a liquid impermeable barrier layer in the middle, i.e. sandwiched by the adhesive sides. Some examples are the Bemis 3916 Sewfree® Tape, which is a heat-activated tape, and the ST-804 thermoplastic adhesive film. In some other embodiments, one or both liquid impermeable layers 124,164 does not have adhesive sides and is bonded to respective layers of the absorbent component 100 by bonding means 110, as described below.

As a result of the moulding process, the liquid impermeable layers 124,164 are bonded together, such as due to melting of the adhesive layers or bonding means 110. The bonded liquid impermeable layers 124,164 form a leakproof pocket containing or enclosing the absorbent layer composite 140, allowing only liquid to enter via the opening 166 for absorption by the absorbent layer composite 140.

Figure 7A:
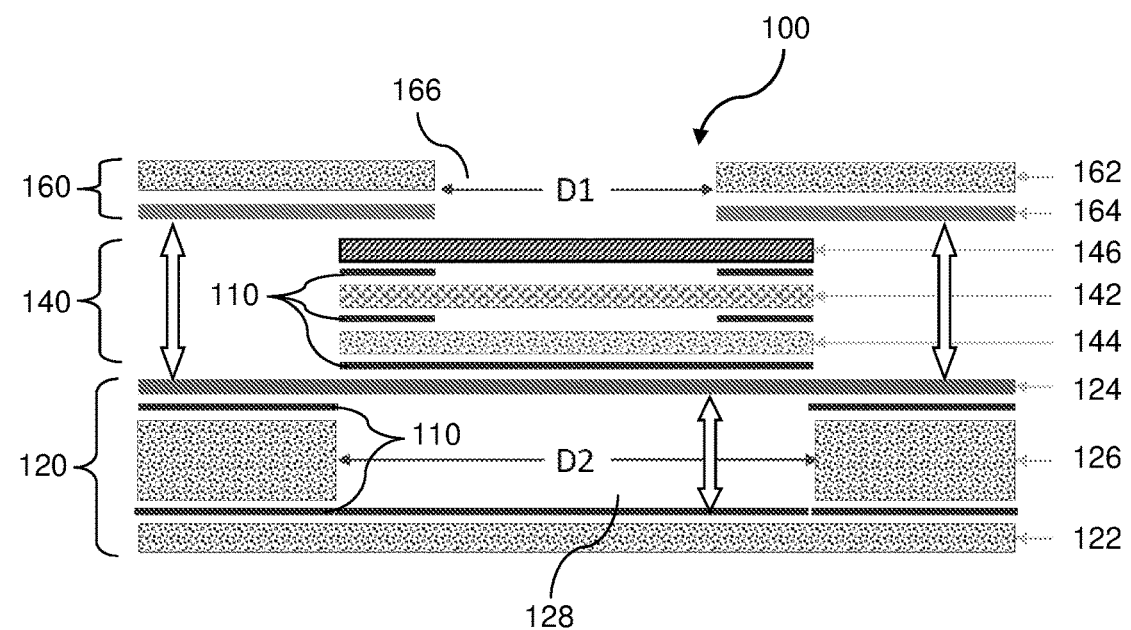
FIG. 7A and FIG. 7B are other cross-sectional illustrations of the absorbent component, in accordance with some embodiments of the present invention.

In some embodiments as shown in FIG. 7A, the first layer composite 120 further includes a third foam layer 126 between the first foam layer 122 and first liquid impermeable layer 124. The third foam layer 126 includes a space 128, i.e. a spatial region or cavity, for containing the absorbent layer composite 140. As such, the space 128 has a shape and overall dimensions corresponding to that of the absorbent layer composite 140. The overall width or diameter of the space 128 is at least D2 and the overall height of the space 128 is at least the overall height of the absorbent layer composite 140, so that the space 128 is able to accommodate the absorbent layer composite 140. The third foam layer 126 is arranged to achieve a more even or uninform overall thickness of the absorbent component 100, since the absorbent layer composite 140 can be fitted into the space 128. The third foam layer 126 may be made of a foam material such as those described above for the one-sided laminated foam layers 122,162 but without the lamination. For example, the third foam layer 126 may be made of bare polyurethane foam.

As described above, the overall dimensions of each of the absorbent fabric layer 142, absorbent foam layer 144, and wicking layer 146 may be the same or may be different such that the absorbent layer composite 140 may have various shapes. Notably, these layers 142,144,146 are dimensioned such that the resultant absorbent layer composite 140 is able to fit into the space 128 so that all the layer composites 120,140,160 can be unified into a single absorbent component 100.

Figure 7B:
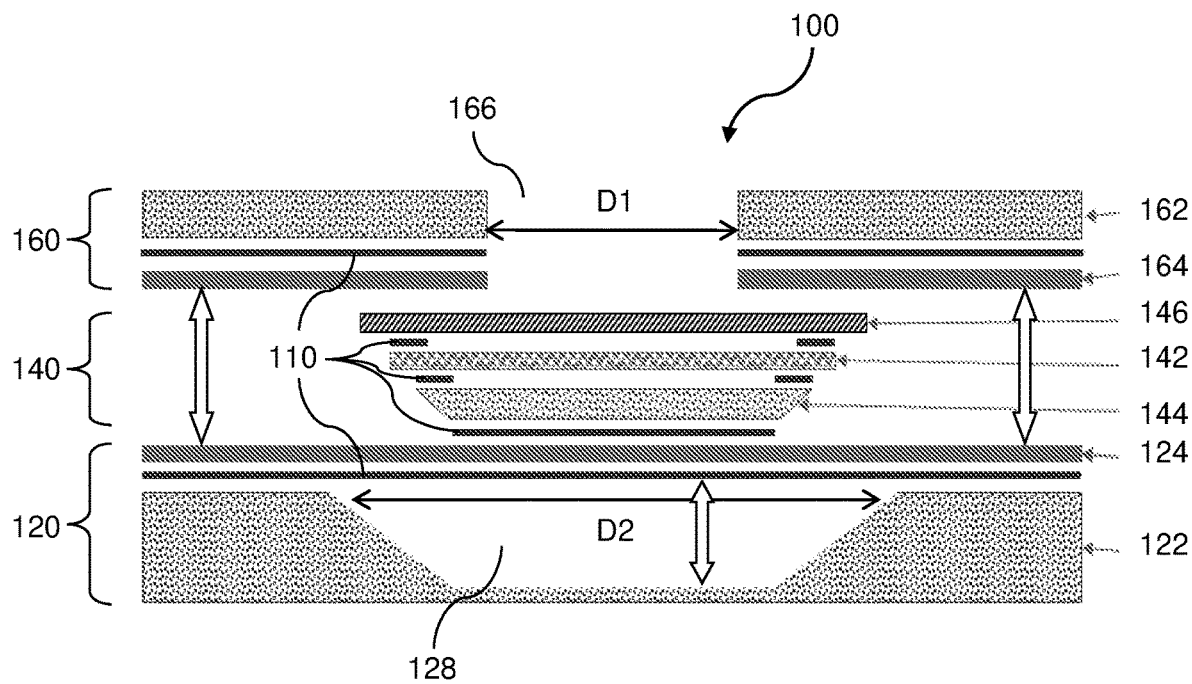

FIG. 7A illustrates the absorbent layer composite 140 with a rectangular cross-sectional shape. Another particular shape that was mentioned is shown in FIG. 7B wherein the absorbent layer composite 140 has a trapeze or trapezium shape. The absorbent layer composite 140 thus has a trapezoidal form wherein its sides are shaved in an angular manner tapering downwards. This trapezoidal form helps to direct bodily fluids towards the centre of the absorbent layer composite 140, thereby reducing the chance of leaks at the edges of the absorbent component 100.

Similarly, in the absorbent component 100 shown in FIG. 7A, the opening 166 and the space 128 have rectangular cross-sectional shapes. The opening 166 and the space 128 may have other shapes or forms such as the trapezium shapes of the absorbent layer composite 140. In an alternative embodiment as shown in FIG. 7B, the absorbent layer composite 140 and the space 128 have trapezoidal forms so that the absorbent layer composite 140 is able to fit into the space 128. As shown in the embodiment of FIG. 7A, the first foam layer 122 and third foam layer 126 are separate foam layers that are bonded together. In an alternative embodiment shown in FIG. 7B, the first foam layer 122 and third foam layer 126 are combined into a single foam layer, which has the same thickness of the bonded combination of the foam layers 122,126. This single foam layer contains a space 128 that functions in the same manner as described above, i.e. for accommodating the absorbent layer composite 140, and the space 128 may be cut or formed in various shapes, including with rectangular or trapezium cross-sections as mentioned above.

In some embodiments, the first layer composite 120 and/or second layer composite 160 further includes at least one outer support layer bonded to the first foam layer 122/second foam layer 162, respectively. The outer support layer is arranged for resisting movement of the absorbent component 100 when used in the garment. Specifically, when the absorbent component 100 is included within the garment, the outer support layer has a gripping/anti-slipping material that grips or clings onto the fabric of the garment to resist movement within the garment. This allows the absorbent component 100 to stay in place within the garment, particularly if the absorbent component 100 is removably inserted into the garment. The material of the outer support layer may include a fabric material, lace fabric, silicone, or an elasticized blend such as Spandex, Lycra, or elastane.

As described above, the absorbent component 100 includes various layers that are bonded together. These layers may be bonded together by bonding means 110 at respective areas of the layers, such as shown in FIG. 7A and FIG. 7B. The bonding means 110 may be an adhesive of bonding agent. For example, the adhesive may be an adhesive tape, liquid glue, or hotmelt powder glue). When the adhesive is an adhesive tape, the tape is a double-sided adhesive tape (such as of the type produced by Bemis Associates Inc.) and said tape may have a single layer or multiple layers where said multiple layers may have one or more functions, such as liquid impermeable layers, elastic layers etc. When the adhesive is a liquid glue, the glue may be a hot melt glue, a liquid resin or combinations thereof (e.g. the adhesive may be a hot melt glue/liquid resin bonding by nozzle extrusion or liquid resin bonding by screen printing/template printing).

In various embodiments of the present invention, there is a method of forming the absorbent component 100, such as shown in FIG. 1A and FIG. 2, for use in a garment. The method includes the step of forming an unmoulded layer composite that includes the first layer composite 120 and absorbent layer composite 140. The method further includes the step of moulding the unmoulded layer composite to thereby form the absorbent component 100. After said moulding, the first foam layer 122 is moulded to shape the absorbent component 100. The absorbent component 100 includes the second liquid impermeable layer 164 bonded to the absorbent layer composite 140 and first layer composite 120 to contain the bodily fluids absorbed by the absorbent layer composite 140.

In some embodiments, the second liquid impermeable layer 164 is bonded to the first foam layer 122. The method includes the step of bonding the second liquid impermeable layer 164 to the absorbent layer composite 140 and first foam layer 122 after moulding the unmoulded layer composite, such that the second liquid impermeable layer 164 forms the peripheral liquid impermeable barrier 180 around the absorbent component 100.

In some embodiments, the unmoulded layer composite includes the second layer composite 160 that includes the second liquid impermeable layer 164 and the second foam layer 162, wherein the opening 166 is formed through the second foam layer 162 and second liquid impermeable layer 164. The method includes the steps of bonding the absorbent layer composite 140 to the first layer composite 120, and bonding the second liquid impermeable layer 164 to the absorbent layer composite 140. After the unmoulded layer composite is moulded, the first and second liquid impermeable layers 124,164 are bonded together and the first and second foam layers 122,162 are moulded to shape the absorbent component 100.

The method may further include one or more of the steps of forming the first layer composite 120, forming the absorbent layer composite 140, and in some embodiments forming the second layer composite 160. It will be appreciated that various aspects of the absorbent component 100 described above apply similarly or analogously to the steps of forming the absorbent component 100, and may not be further described for purpose of brevity.

An embodiment of the method is described for forming the absorbent component 100 as shown in FIG. 7A. The method includes forming the first layer composite 120, forming the absorbent layer composite 140, and forming the second layer composite 160.

Steps of forming the second layer composite 160 are described as follows. Temporarily attach the second liquid impermeable layer 164 to the second foam layer 162. Cut out the opening 166 being a circle of diameter D1 through the second foam layer 162 and second liquid impermeable layer 164.

Steps of forming the absorbent layer composite 140 are described as follows. Cut respective materials for the absorbent fabric layer 142, absorbent foam layer 144, and wicking layer 146, each being a circle of size D2. Demarcate bonding-exclusion areas on each of the absorbent fabric layer 142, absorbent foam layer 144, and wicking layer 146. Cover the bonding-exclusion areas with a circular sheet for each of the absorbent fabric layer 142, absorbent foam layer 144, and wicking layer 146. Apply the bonding means 110 on each of the absorbent fabric layer 142, absorbent foam layer 144, and wicking layer 146, excluding the respective bonding-exclusion areas due to the circular sheets. Remove the circular sheets from the absorbent fabric layer 142, absorbent foam layer 144, and wicking layer 146. Place the absorbent fabric layer 142 on top of the absorbent foam layer 144. Place the wicking layer 146 on top of the absorbent fabric layer 142.

Steps of forming the first layer composite 120 are described as follows. Cut out the space 128 through the third foam layer 126. The space 128 is circular having a size of at least D2 to accommodate the absorbent layer composite 140. Apply the bonding means 110 on one side of the first foam layer 122. Place one side of the third foam layer 126 on top of the first foam layer 122 and attach them together by the bonding means 110 applied on the one side of the first foam layer 122. Apply the bonding means 110 on the other side of the third foam layer 126. Attach the third foam layer 126 to the first liquid impermeable layer 124.

The three layer composites 120,140,160 are then combined to form the unmoulded layer composite, as follows. Apply the bonding means 110 on the absorbent foam layer 144 for bonding to the first liquid impermeable layer 124. Attach the absorbent layer composite 140 to the first layer composite 120. Apply the bonding means 110 on the wicking layer 146 for bonding to the second liquid impermeable layer 164. Attach the second layer composite 160 to the absorbent layer composite 140.

Figure 8A:
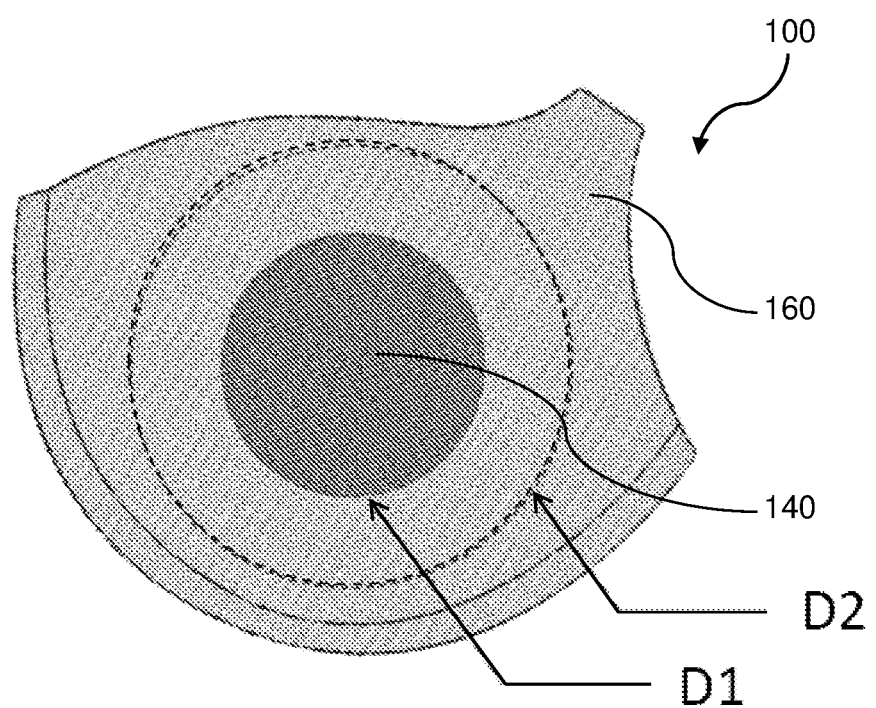
FIG. 8A and FIG. 8B are sketch illustrations of the absorbent component of FIG. 7A, in accordance with some embodiments of the present invention.
Figure 8B:
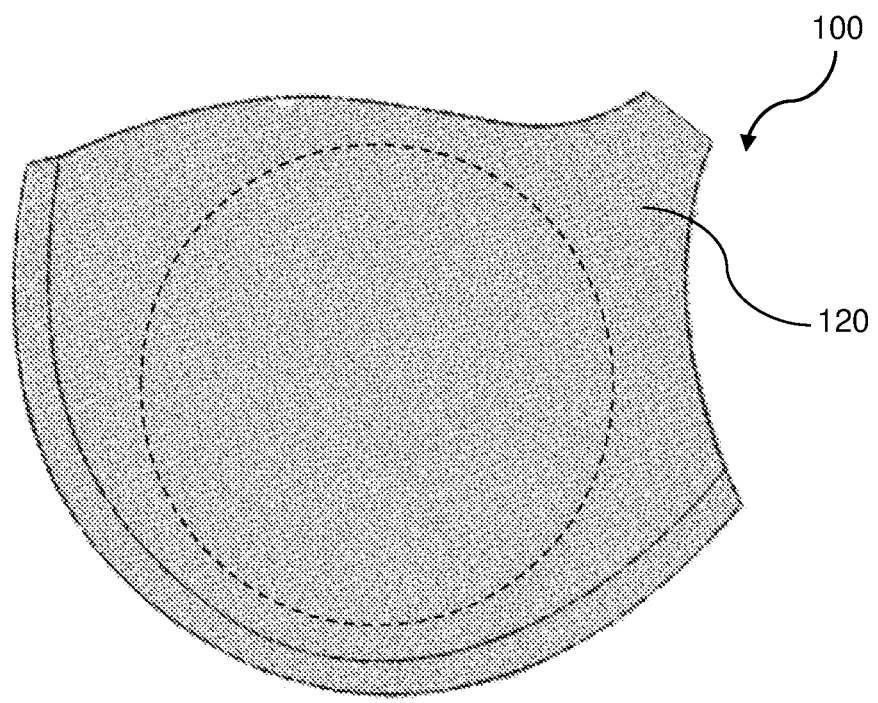
Figure 9A:
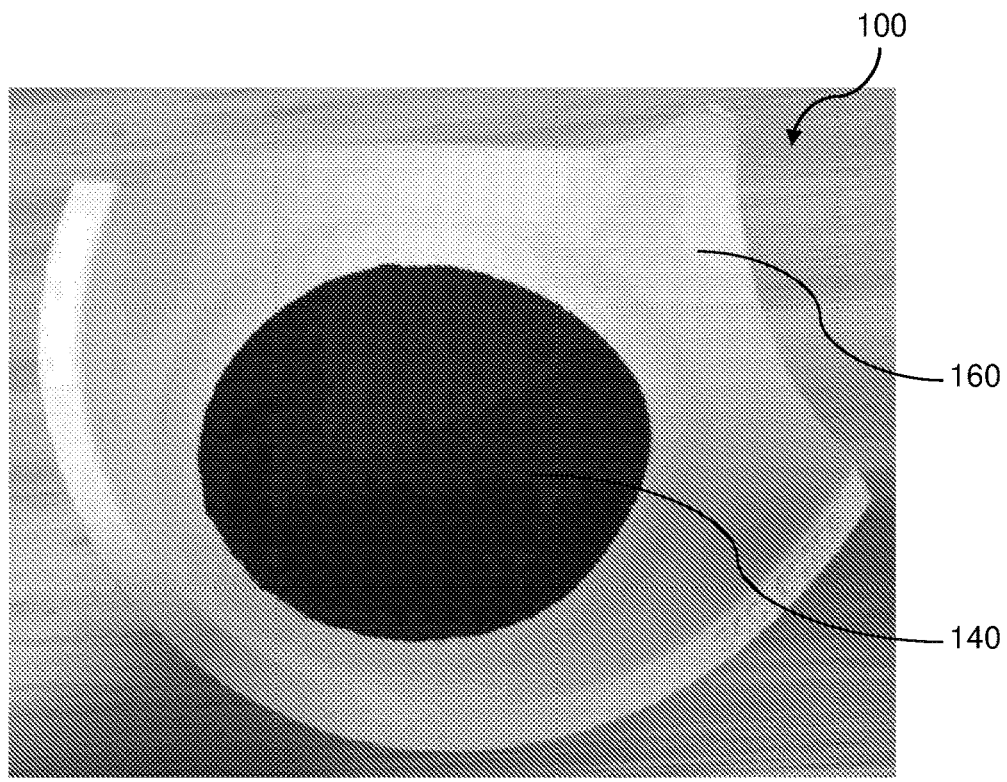
FIG. 9A and FIG. 9B are photographs of the absorbent component of FIG. 7A, in accordance with some embodiments of the present invention.
Figure 9B:
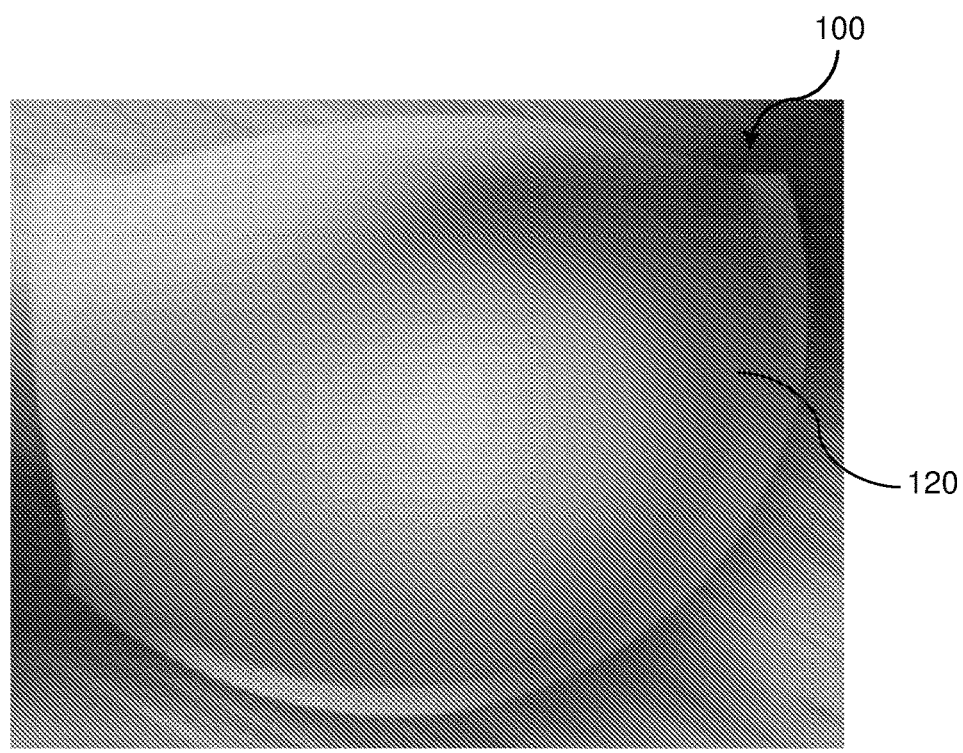

The method further includes moulding the unmoulded layer composite in a moulding process to form the absorbent component 100. The conditions of the moulding process are a temperature of approximately 180° C. to 185° C., a pressure of approximately 6 bars, and a dwelling time or moulding duration of approximately 150 seconds. FIG. 8A and FIG. 8B illustrate sketches of the inside and outside of the moulded absorbent component 100, respectively. FIG. 9A and FIG. 9B illustrate photographs of the inside and outside of the moulded absorbent component 100, respectively.

Figure 10A:
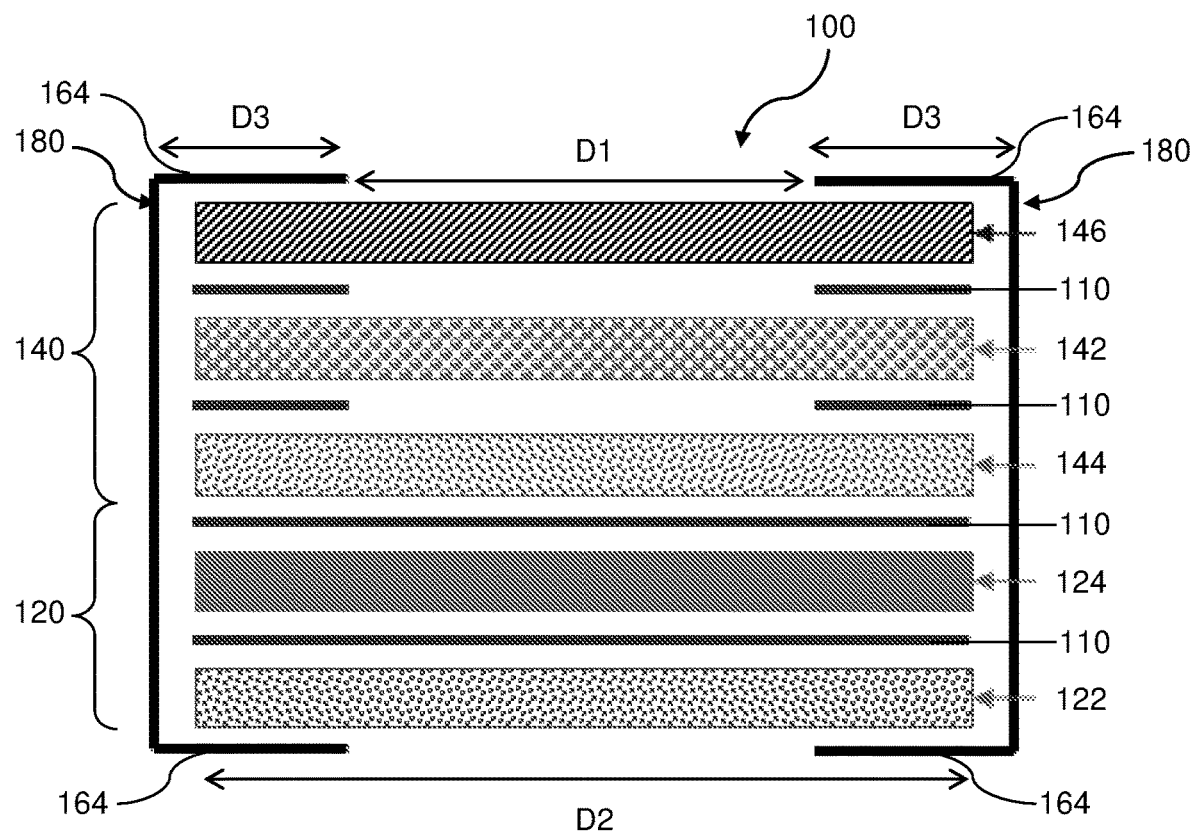
FIG. 10A to FIG. 10C are other cross-sectional illustrations of the absorbent component, in accordance with some embodiments of the present invention.

An embodiment of the method is described for forming the absorbent component 100 as shown in FIG. 10A. The method includes forming the first layer composite 120 and forming the absorbent layer composite 140.

Steps of forming the first layer composite 120 are described as follows. Apply the bonding means 110 on one side of the first foam layer 122. Attach the first liquid impermeable layer 124 to the first foam layer 122 via the bonding means 110. Steps of forming the absorbent layer composite 140 are similar to the aforementioned steps. Particularly, the absorbent layer composite 140 includes the absorbent fabric layer 142, absorbent foam layer 144, and wicking layer 146.

The two layer composites 120,140 are then combined to form the unmoulded layer composite, as follows. Apply the bonding means 110 on the absorbent foam layer 144 for bonding to the first liquid impermeable layer 124. Attach the absorbent layer composite 140 to the first layer composite 120.

The method further includes moulding the unmoulded layer composite in the moulding process to form the absorbent component 100, similar to the moulding process described above. The method further includes bonding the second liquid impermeable layer 164 to the absorbent layer composite 140 and first foam layer 122 after moulding the unmoulded layer composite, such that the second liquid impermeable layer 164 forms the peripheral liquid impermeable barrier 180 around the absorbent component 100. The second liquid impermeable layer 164 may overlap with the absorbent layer composite 140 and first foam layer 122 by a length D3, which may be 10 mm for example.

Although the second liquid impermeable layer 164 is bonded after moulding, it may be possible that the second liquid impermeable layer 164 is bonded before moulding. In this case, the combination of the layer composites 120,140 and the second liquid impermeable layer 164 are subjected to the moulding process.

Figure 11A:
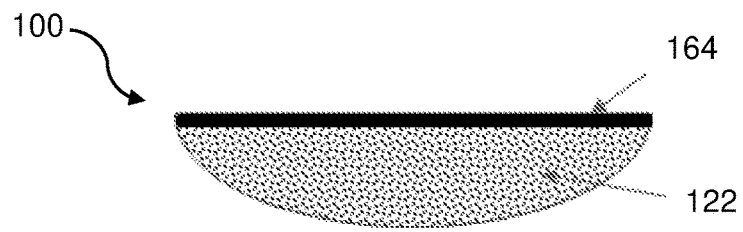
FIG. 11A to FIG. 11C are sketch illustrations of the absorbent component of FIG. 10A, in accordance with some embodiments of the present invention.
Figure 11B:
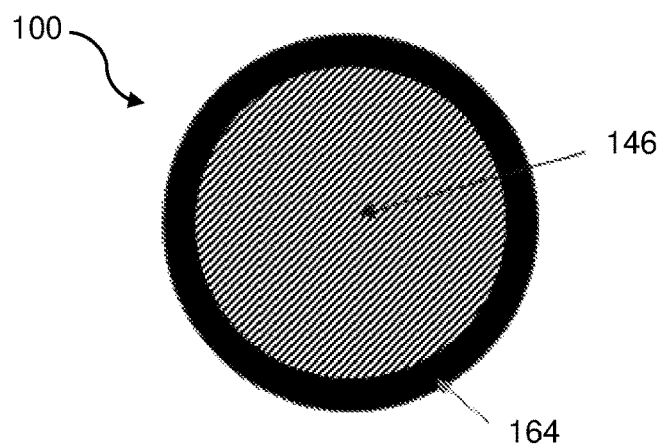
Figure 11C:
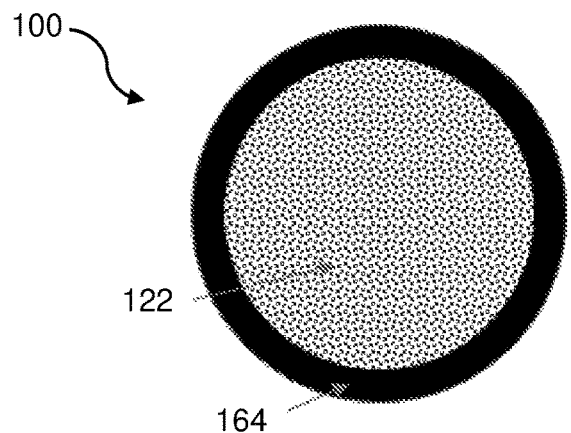
Figure 12A:
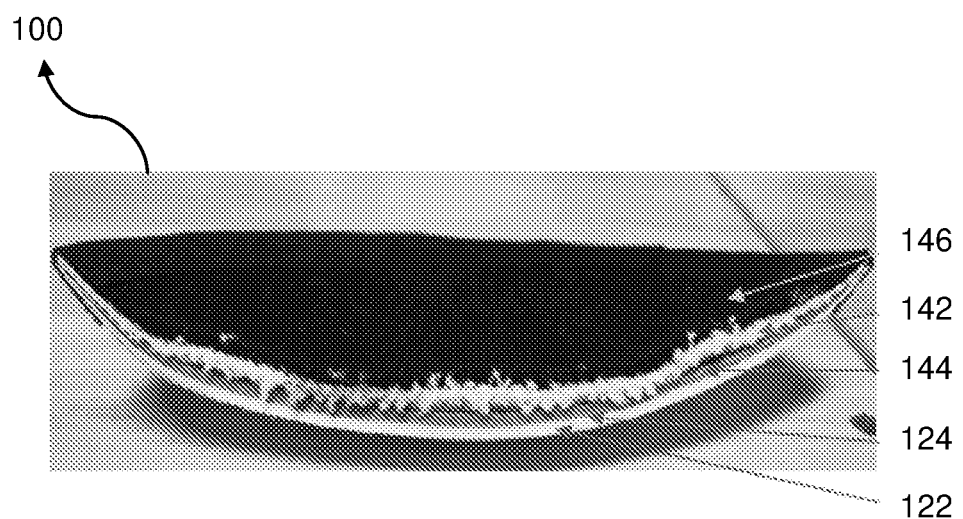
FIG. 12A to FIG. 12D are photographs of the absorbent component of FIG. 10A, in accordance with some embodiments of the present invention.
Figure 12B:
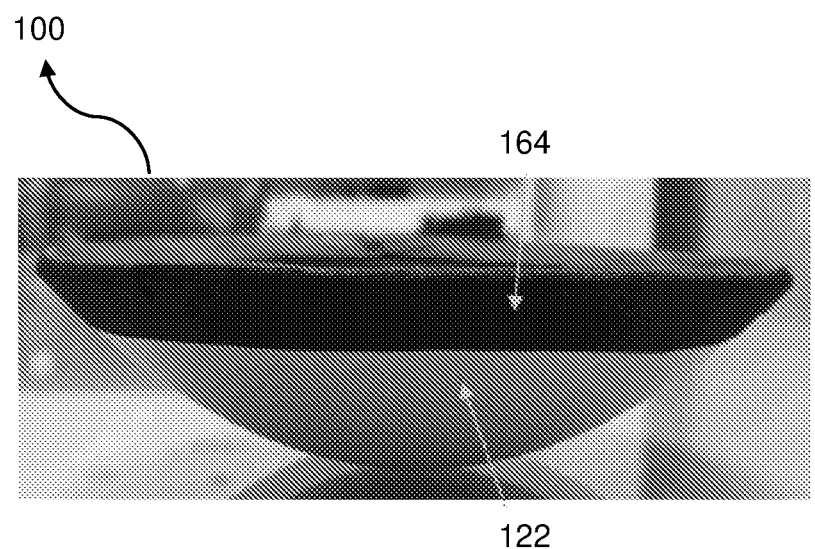
Figure 12C:
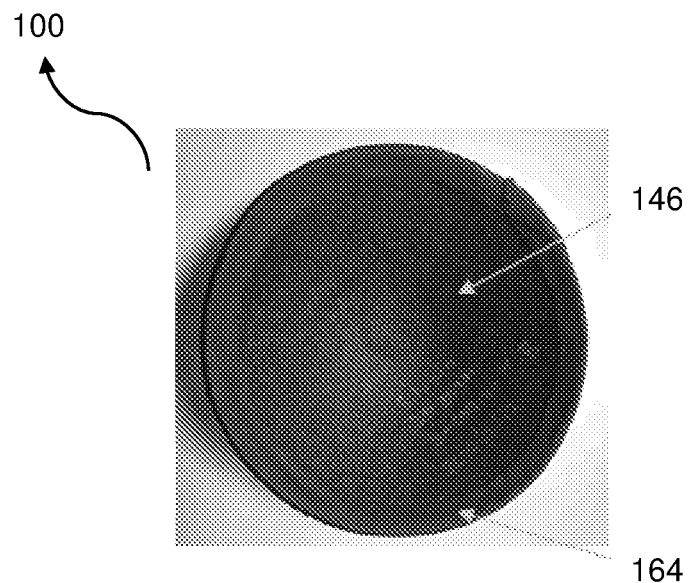
Figure 12D:
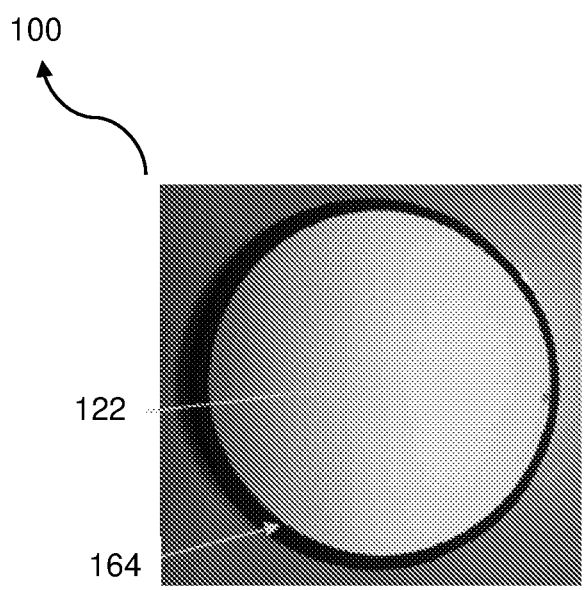

FIG. 11A to FIG. 11C illustrate sketches of the exterior side, inside, and outside of the moulded absorbent component 100, respectively. FIG. 12A to FIG. 12D illustrate photographs of the cross-sectional side, exterior side, inside, and outside of the moulded absorbent component 100, respectively.

Figure 10B:
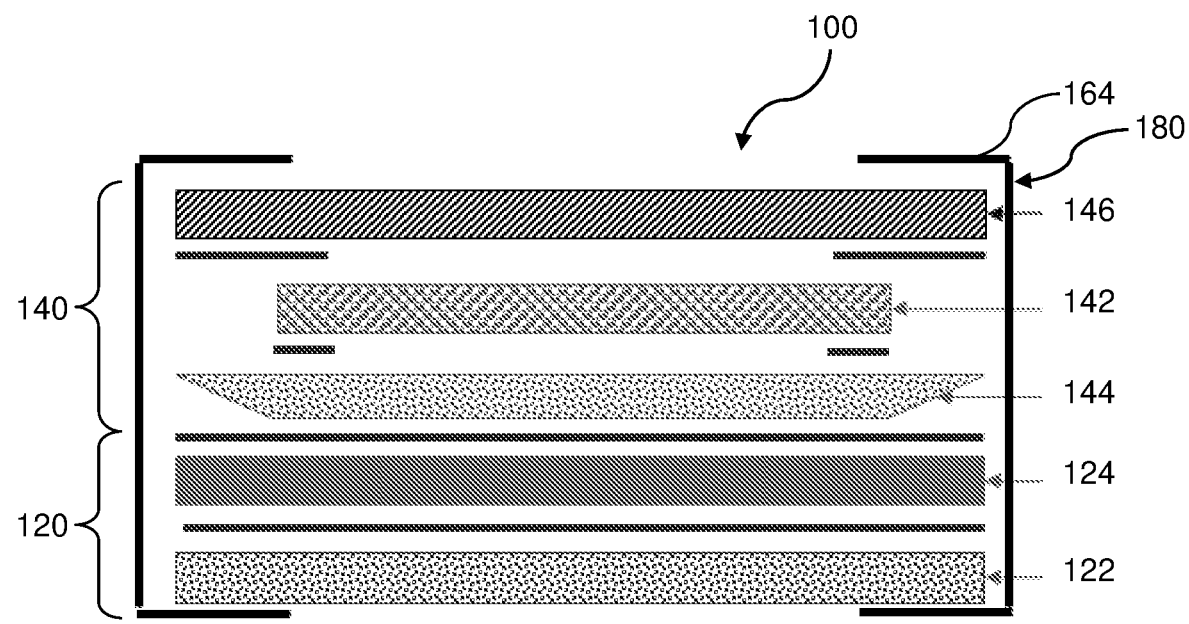
Figure 10C:
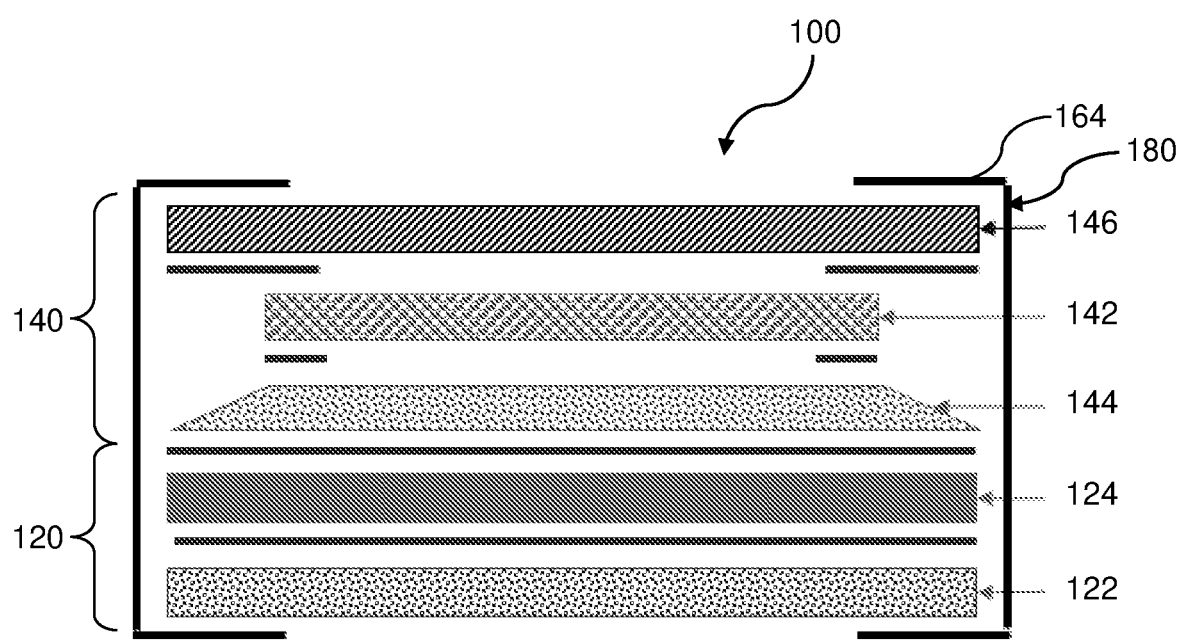

FIG. 10A illustrates the absorbent layer composite 140 wherein the absorbent fabric layer 142, absorbent foam layer 144, and wicking layer 146 have the same overall dimensions and similar rectangular cross-sectional shapes. As mentioned above, the dimensions and/or cross-sectional shapes may be different. In another embodiment as shown in FIG. 10B, the absorbent fabric layer 142 is smaller than the wicking layer 146 and absorbent foam layer 144. Further, the absorbent foam layer 144 has a trapezium cross-sectional shape wherein its sides are shaved in an angular manner tapering downwards. In yet another embodiment as shown in FIG. 10C, the absorbent foam layer 144 has an inverse trapezium cross-sectional shape wherein its sides are shaved in an angular manner tapering upwards. It will be appreciated that one or more layers of the absorbent layer composite 140 can be sized and shaped accordingly as desired.

In various embodiments of the present invention, there is a garment and a method of forming the garment including the absorbent component 100. The garment includes a fabric body configured to be worn by the user, and the absorbent component 100 is included within the fabric body. Particularly, the fabric body has a portion, such as an internal portion thereof, for including the absorbent component 100. In one embodiment, the absorbent component 100 is included within the fabric body such that it is integrally formed with the fabric body, such as by adhering, gluing, or stitching the absorbent component 100 to the fabric body. It will be appreciated that there may be other means, such as fastening means, to integrally form the absorbent component 100 within the fabric body. In another embodiment, the absorbent component 100 is removably inserted into the fabric body, such as for replacement of the absorbent component 100 without replacing the entire fabric body or garment. The absorbent component 100 being removable from the fabric body allows for replacement of the absorbent component 100 with a new one, such as if the current one is soaked with bodily fluids.

In the method of forming the garment, the method includes the step of forming the fabric body of the garment configured to be worn by a user. The method further includes the step of forming the absorbent component 100 for use in the garment. Said forming of the absorbent component 100 includes the steps described above and will not be further described for purpose of brevity. The method further includes the step of including the absorbent component 100 within the fabric body. In one embodiment, the absorbent component 100 is included by integrally forming the fabric body with the absorbent component 100. In another embodiment, the absorbent component 100 is included by removably inserting it into the fabric body. The absorbent component 100 is positioned such that when the user wears the garment, the absorbent component 100 is in direct contact with the user's skin for absorption of bodily fluids.

The garment may be an intimate garment or undergarment worn by a user particularly at parts of the body where there may be excretions of bodily fluids. For example, the garment may be, but is not limited to brassieres, lingerie, sportswear, and similar close-fitting or form-fitting garments. More specifically, the garment may be a nursing bra, nursing tops, nursing cup, nursing pad, bra cup, bra pad, shelf bra, a top with built-in bra cups, sports bras, and workout tops. Such garments may be included with the absorbent component 100 for absorption of bodily fluids such as breast milk and sweat. Particularly, the absorbent component 100 may be a nursing component for use in a postpartum garment such as a nursing bra or top. In another use case, the garment may be a postoperative garment worn by patients after surgery, such as a post-surgery support bra for patients after undergoing mastectomy.

In some embodiments, the absorbent component 100 and/or garment may be made to be washable and reusable, thereby helping to reduce environmental impact. For example, the absorbent component 100/garment is able to withstand at least 30 (e.g. a minimum of 50 or 100) machine wash and tumble dry cycles without risk of delamination, change in overall appearance, and integrity of the various layers and liquid management parameters as discussed herein. The material selection and unique construction ensures that the absorbent component 100/garment are washable without compromising on moisture management. Further, the integrity of the absorbent component 100 may be maintained for a minimum of 30 (e.g. a minimum of 50 or 100) wash and dry cycles. This ensures that the absorbent component 100 will not leak during the lifetime of the garment. For example, the various layer composites 120, 140, 160 of the absorbent component 100 mentioned herein were chosen such that they remain chemically, thermally and mechanically stable throughout the intended lifetime of the absorbent component 100/garment while undergoing up to 30 (e.g. up to 50 or up to 100) wash and dry cycles.

Various parts, including the layer composites 120, 140, 160, layers thereof, and bonding means 110, of the absorbent component 100 may be made of a material that is heat stable up to at least 190° C. This heat stability enables the absorbent component 100 to be used in a garment that can be washed and dried multiple times. Unless otherwise specified, used herein, the term "heat stable" is intended to stipulate that there is no change in the physical state of the part in question after being subjected to the stated temperature for a period of time consistent with a machine drying cycle. Additionally, the heat stability of the materials allow the various parts of the absorbent component 100 to withstand moulding and retain their properties, such as wicking and absorbent capacity, particularly because the moulding process requires a temperature of approximately 180° C. to 185° C.

The absorbent component 100 according to the present invention thus provides a moulded, absorbent, and leak-proof product useable in a garment, such as a nursing bra, which can be used to absorb bodily fluids such as breast milk and sweat. The absorbent component 100 is also reusable so that once the user has finished wearing the garment, the garment can be washed together with the absorbent component 100 to remove the absorbed bodily fluids. The absorbent component 100 may be integrally formed in the garment or may be removably inserted into the garment to allow for replacement and use in other garments.

As the absorbent component 100 is moulded, it can be adapted to the shape of the garment and/or body part where the garment is worn. For example, the absorbent component 100 is used in a nursing bra and it is moulded and shaped to conform to the breast and bra shape. The absorbent component 100 thus achieves a structured shape that allows it to lie substantially flat when used in the bra, making it less visible through the bra. This avoids embarrassment to the user and expands clothing options for the user. Additionally, the structured shape of the absorbent component 100 makes the absorbent component 100 feel like a normal bra cup which the wearer is already familiar with, thus making the garment easier to wear.

The absorbent capacity of the absorbent component 100 is higher than current products in the market targeting breast milk leakage, such as removable bra pads used in postpartum garments or nursing bras. Current bra pads tend to remain wet on the surface due to poor wicking and cause an uncomfortable feeling of wetness to the user. The absorbent capacity of current bra pads is also very low. For example, some of them are able to absorb only less than 13 ml. Based on a survey with nursing mothers, the production of breast milk per day is approximately 800 ml on average, and approximately between 10 and 80 ml (with average of approximately 30 ml) of breast milk leaks during a period of 12 hours. The current bra pads are thus unable to absorb and withhold the leaked breast milk, resulting in leakages from the bottom and sides of the bra pads, thereby causing embarrassment to the user as the breast milk leaks onto their garments and clothes and becomes visible from the outside. Another reason for breast milk leakage through the garments and clothes is the current bra pads tend not to stay in place within the bras, thereby preventing them from properly absorbing the breast milk directly from the breasts.

As described above, the absorbent capacity of the absorbent component 100 is at least 30 ml which allows the absorbent component 100 to feel dry to the user and still able to absorb enough bodily fluids to last through the day. The absorbed bodily fluids do not leak through the absorbent component 100, thereby avoiding embarrassment to the user. Various tests have been performed on the absorbent component 100 on their absorbency, wetness, and leak-proof properties. The results of these tests showed that these properties of the absorbent component 100 surpassed that of existing products in the market.

Some tests were performed on a wicking fabric material for the wicking layer 146, and the wicking fabric is made of 100% polyester. The tests were performed on two samples of the wicking fabric, the first being an untreated sample and the second being a sample that is treated with a hydrophilic agent, specifically 30 g/l of FERAN® ICE. Results of the tests are shown in FIG. 13A to FIG. 13D. Some of the samples were subjected to multiple wash cycles at 60° C., and also to the moulding process before or after washing. The test results showed that by treating the wicking fabric with the hydrophilic agent, the wicking and absorbent efficacy improved significantly and the efficacy do not diminish even if the wicking fabric is subjected to multiple wash cycles and/or the moulding process.

Another set of tests was performed on five samples of the wicking fabric. These wicking fabric samples were treated with varying compositions of finishing agents, including an anti-microbial or anti-bacterial agent RUCO®-BAC AGP, a hydrophilic agent FERAN® ICS, an anti-static agent RUCO®-STAD ADM, and a technical finishing agent RUCO®-PUR SLR to improve technical properties of the wicking fabric. The wicking fabric samples were further treated with a pH4.5 citric acid compound. The varying compositions of the finishing agents for these samples are shown in FIG. 13E. The samples were subjected to multiple wash cycles at 60° C. and the tests were performed to evaluate the anti-microbial properties of the samples based on two bacteria species—*Staphylococcus aureus* and *Klebsiella pneumoniae*. The samples were exposed to the bacteria separately for 20 hours at a temperature of 37° C. The test results in FIG. 13E showed that the anti-microbial properties of the samples reduced the bacteria by approximately 99%, even after 50 wash cycles. In other words, the anti-microbial properties do not diminish even if the wicking fabric is subjected to multiple wash cycles.

An absorbency test was performed to evaluate the absorbent capacity of the absorbent component 100. The test was performed from 0930 hours to 1730 hours to evaluate how much liquid the absorbent component 100 was able to absorb. The test results in FIG. 13F showed that the absorbent component 100 was able to absorb approximately up to 30 ml of liquid over a duration of approximately 6 hours before leakages start to appear. Accordingly, the absorbent component 100 is able to achieve a high absorbent capacity of at least 30 ml, higher than those of current bra pads.

Further aspects and embodiments of the invention may relate to an adsorbent component as depicted in FIG. 14A and FIGS. 15A to 15C.

At its most basic, the embodiment of FIG. 14A and FIGS. 15A to 15C requires a first layer composite 120 comprising a first foam layer 122 and a first liquid impermeable layer 124 and an absorbent layer composite 140 bonded to the first liquid impermeable layer for absorbing bodily fluids and the first foam layer is moulded to shape the absorbent component. The first liquid impermeable layer 124 forms a liquid-impenetrable barrier between the first foam layer 122 and the absorbent layer composite 140. In addition, the first liquid impermeable layer 124, the first foam layer 122 and the absorbent layer composite 140 each have one or more edges, such that none of the edges of the first fluid impenetrable layer 124 extends beyond the edges of the first foam layer 122 and the edges of the absorbent layer composite 140 to thereby form an edge seal. In particular embodiments that may be mentioned herein, this component may be provided in the form of a nursing pad, though its inclusion in a bra may be contemplated.

As will be appreciated, the layers described above are held together by bonding means 110, which can be any bonding means described hereinbefore.

When used herein, the term "edge seal" will be understood to mean that the first liquid impermeable layer 124 is formed so that it does not cover the edge of the absorbent layer composite 140 or the edge of the first foam layer 122. When used herein "edge" refers to the height dimension of the layer. This may be achieved by cutting the layers so that they have the same footprint, or by making the first liquid impermeable layer 124 smaller than one of the first foam layer 122 and the absorbent layer composite 140 (i.e. smaller than the first foam layer 122), such that it is entirely bonded to the surface of the layer with the larger footprint.

The first foam layer 122 and the first liquid impermeable layer 124 may be formed from the materials described hereinbefore. The absorbent layer composite 140 may be formed from a combination of a superabsorbent foam 144 and an absorbent fabric 142 as described hereinbefore. As depicted, in FIG. 14A, embodiments of this type may also include a wicking fabric 146 bonded to the absorbent layer composite 140. The wicking fabric may be formed from suitable materials described hereinbefore.

Figure 14B:
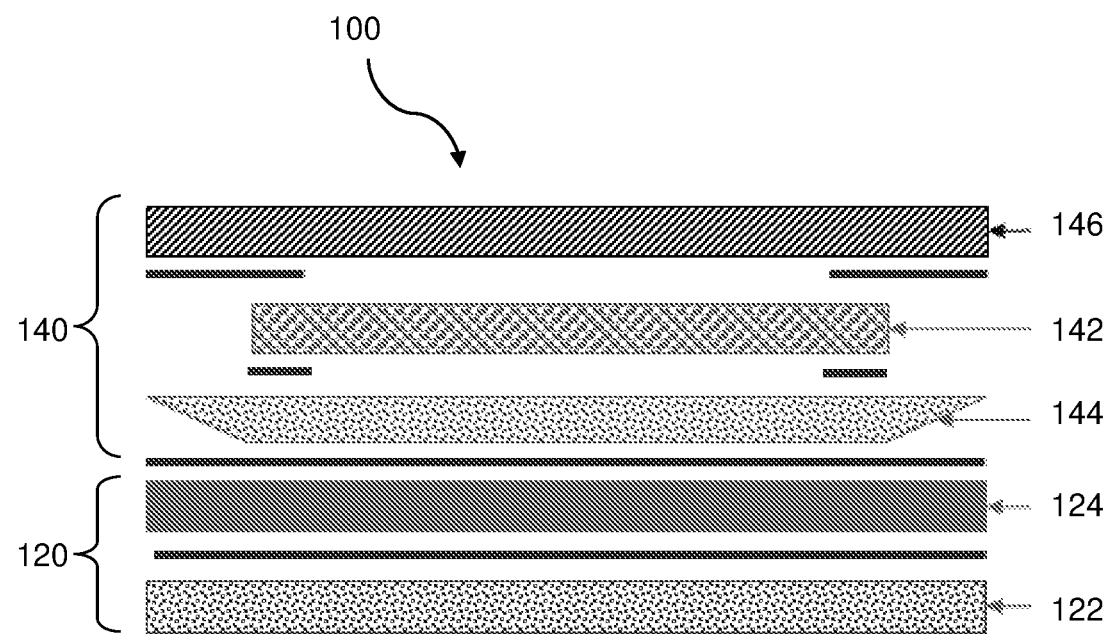
Figure 14C:
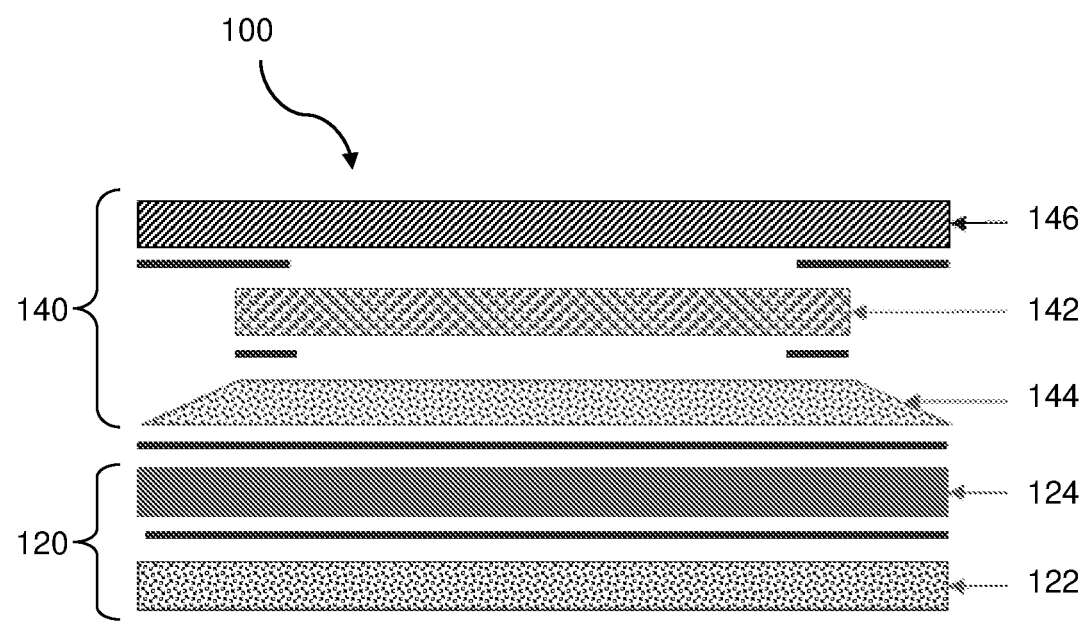
Figure 15A:
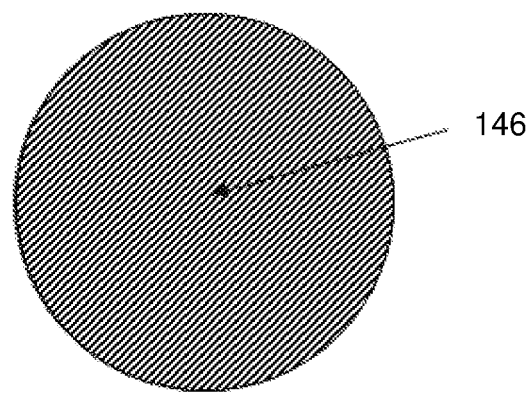
FIG. 15A to FIG. 15C are sketch illustrations of the absorbent component of FIG. 14A.
Figure 15B:
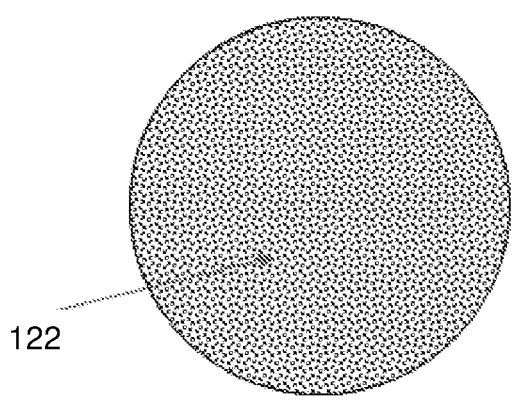
Figure 15C:
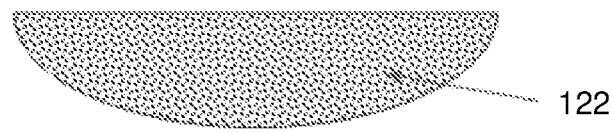

FIG. 14A illustrates the absorbent layer composite 140 wherein the absorbent fabric layer 142, absorbent foam layer 144, and wicking layer 146 have the same overall dimensions and similar rectangular cross-sectional shapes. As mentioned above, the dimensions and/or cross-sectional shapes may be different. In another embodiment as shown in FIG. 14B, the absorbent fabric layer 142 is smaller than the wicking layer 146 and absorbent foam layer 144. Further, the absorbent foam layer 144 has a trapezium cross-sectional shape wherein its sides are shaved in an angular manner tapering downwards. In yet another embodiment as shown in FIG. 14C, the absorbent foam layer 144 has an inverse trapezium cross-sectional shape wherein its sides are shaved in an angular manner tapering upwards. It will be appreciated that one or more layers of the absorbent layer composite 140 can be sized and shaped accordingly as desired.

The absorbent component 100 and garments, such as bras, using the absorbent component 100 are suitable for working and/or nursing mothers who need to be out of their homes. The absorbent component 100 is moulded to retain the breast shape while also providing high absorbent capacity and while safety of no leaks showing through their clothes. In some countries such as the United States, new mothers are given limited maternity leave, such as 2 weeks, and have to return to work shortly after childbirth. The absorbent component 100 and garments using it would thus be suitable for these new mothers who have a need for functional nursing bras that also look and feel like normal bras.

In the foregoing detailed description, embodiments of the present invention in relation to an absorbent component 100 for use in a garment are described with reference to the provided figures. The description of the various embodiments herein is not intended to call out or be limited only to specific or particular representations of the present invention, but merely to illustrate non-limiting examples of the present invention. The present invention serves to address at least one of the mentioned problems and issues associated with the prior art. Although only some embodiments of the present invention are disclosed herein, it will be apparent to a person having ordinary skill in the art in view of this invention that a variety of changes and/or modifications can be made to the disclosed embodiments without departing from the scope of the present invention. Therefore, the scope of the invention as well as the scope of the following claims is not limited to embodiments described herein.

The invention claimed is:

1. An absorbent component for use in a garment, the absorbent component comprising:
   a first layer composite comprising a first foam layer and a first liquid impermeable layer;
   an absorbent layer composite bonded to the first liquid impermeable layer for absorbing bodily fluids; and
   a second liquid impermeable layer bonded to the absorbent layer composite and first layer composite to contain the bodily fluids absorbed by the absorbent layer composite,
   wherein the second liquid impermeable layer forms an opening for receiving the bodily fluids to the absorbent layer composite; and
   wherein the first foam layer is moulded to shape the absorbent component, and the absorbent component is washable and reusable.

2. The component according to claim 1, wherein the first and second liquid impermeable layers are bonded together.

3. The component according to claim 2, further comprising a second layer composite comprising the second liquid impermeable layer and a second foam layer,
   wherein the opening is formed through the second foam layer and second liquid impermeable layer; and
   wherein the first and second foam layers are moulded to shape the absorbent component.

4. The component according to claim 3, wherein the first layer composite further comprises a third foam layer between the first foam layer and first liquid impermeable layer, the third foam layer comprising a space for containing the absorbent layer composite.

5. The component according to claim 4, wherein the third foam layer comprises bare polyurethane foam.

6. The component according to claim 1, further comprising at least one outer support layer bonded to the first layer composite, the outer support layer for resisting movement of the component when used in a garment.

7. The component according to claim 1, wherein one or more of the following apply:
   (a) the absorbent layer composite comprises a wicking layer bonded to the second liquid impermeable layer for receiving the bodily fluids;
   (b) the absorbent layer composite comprises an outer softening layer; and
   (c) the second liquid impermeable layer is bonded to the first foam layer to form a peripheral liquid impermeable barrier around the absorbent component.

8. The component according to claim 1, wherein the component is useable in a maternity and/or postpartum garment for nursing.

9. A method of forming a washable and reusable absorbent component for use in a garment, the method comprising:
   forming an unmoulded layer composite comprising:
      a first layer composite comprising a first foam layer and a first liquid impermeable layer; and
      an absorbent layer composite bonded to the first liquid impermeable layer for absorbing bodily fluids; and
   moulding the unmoulded layer composite to thereby form the absorbent component, the absorbent component comprising a second liquid impermeable layer bonded to the absorbent layer composite and first layer composite to contain the bodily fluids absorbed by the absorbent layer composite,
   wherein the second liquid impermeable layer forms an opening for receiving the bodily fluids to the absorbent layer composite; and
   wherein the first foam layer is moulded to shape the absorbent component.

10. The method according to claim 9, further comprising bonding the second liquid impermeable layer to the absorbent layer composite and first foam layer after moulding the unmoulded layer composite, such that the second liquid impermeable layer forms a peripheral liquid impermeable barrier around the absorbent component.

11. The method according to claim 9, wherein the unmoulded layer composite further comprises a second layer composite comprising the second liquid impermeable layer and a second foam layer, the opening formed through the second foam layer and second liquid impermeable layer, wherein said forming of the unmoulded layer composite comprises:
   bonding the absorbent layer composite to the first layer composite; and
   bonding the second liquid impermeable layer to the absorbent layer composite,
   wherein after moulding, the first and second liquid impermeable layers are bonded together and the first and second foam layers are moulded to shape the absorbent component.

12. The method according to claim 9, wherein one or both of the following apply:
   (a) the method further comprises forming the absorbent layer composite comprising an absorbent fabric layer and/or an absorbent foam layer for absorbing the bodily fluids; or
   (b) the component is useable in a maternity and/or postpartum garment for nursing.

13. The method according to claim 12, wherein the absorbent layer composite comprises the absorbent fabric layer, absorbent foam layer, and a wicking layer bonded to the second liquid impermeable layer for receiving the bodily fluids.

14. The method according to claim 13, said forming of the absorbent layer composite comprising:
   attaching the absorbent fabric layer to the absorbent foam layer; and
   attaching the wicking layer to the absorbent fabric layer, such that the absorbent fabric layer interposes the wicking layer and absorbent foam layer.

15. A garment comprising:
   a fabric body configured to be worn by a user; and
   an absorbent component for including within the fabric body, the absorbent component comprising:
      a first layer composite comprising a first foam layer and a first liquid impermeable layer;
      an absorbent layer composite bonded to the first liquid impermeable layer for absorbing bodily fluids; and
      a second liquid impermeable layer bonded to the absorbent layer composite and first layer composite to contain the bodily fluids absorbed by the absorbent layer composite,
      wherein the second liquid impermeable layer forms an opening for receiving the bodily fluids to the absorbent layer composite; and
      wherein the first foam layer is moulded to shape the absorbent component,
   and wherein the absorbent component is washable and reusable.

16. The garment according to claim 15, wherein the garment is a maternity and/or postpartum garment.

17. The garment according to claim 15, wherein the garment is a postoperative garment for mastectomy patients.

18. A method of forming a garment, comprising:
forming a fabric body of the garment configured to be worn by a user;
forming a washable and reusable absorbent component for use in the garment, comprising:
    forming an unmoulded layer composite comprising:
        a first layer composite comprising a first foam layer and a first liquid impermeable layer; and
        an absorbent layer composite bonded to the first liquid impermeable layer for absorbing bodily fluids; and
    moulding the unmoulded layer composite to thereby form the absorbent component, the absorbent component comprising a second liquid impermeable layer bonded to the absorbent layer composite and first layer composite to contain the bodily fluids absorbed by the absorbent layer composite; and
including the absorbent component within the fabric body,
wherein the second liquid impermeable layer forms an opening for receiving the bodily fluids to the absorbent layer composite; and
wherein the first foam layer is moulded to shape the absorbent component.

19. The method according to claim 18, wherein the garment is a maternity and/or postpartum garment.

20. An absorbent component for use in a garment, the absorbent component comprising:
a first layer composite comprising a first foam layer and a first liquid impermeable layer, each of the first foam layer and the first liquid impermeable layer comprising one or more edges; and
an absorbent layer composite bonded to the first liquid impermeable layer for absorbing bodily fluids, the absorbent layer composite comprising one or more edges,
wherein the first liquid impermeable layer forms a liquid-impenetrable barrier between the first foam layer and the absorbent layer composite;
wherein none of the edges of the first liquid impermeable layer extends beyond the edges of the first foam layer and the absorbent layer composite to form an edge seal;
wherein the first foam layer is moulded to shape the absorbent component; and
wherein the absorbent component is washable and reusable.

* * * * *